(12) United States Patent
Chin et al.

(10) Patent No.: US 8,734,452 B2
(45) Date of Patent: May 27, 2014

(54) GUIDANCE SYSTEM, TOOLS AND DEVICES FOR SPINAL FIXATION

(75) Inventors: Kingsley Richard Chin, West Palm Beach, FL (US); Christopher A. Chang, Beverly, MA (US); Ernie Corrao, Bethel, CT (US)

(73) Assignee: Spinefrontier, Inc, Beverly, MA (US)

( * ) Notice: Subject to any disclaimer, the term of this patent is extended or adjusted under 35 U.S.C. 154(b) by 1404 days.

(21) Appl. No.: 11/955,621

(22) Filed: Dec. 13, 2007

(65) Prior Publication Data

US 2008/0147079 A1 Jun. 19, 2008

Related U.S. Application Data

(63) Continuation-in-part of application No. 11/779,526, filed on Jul. 18, 2007, now Pat. No. 8,002,799.

(60) Provisional application No. 60/870,251, filed on Dec. 15, 2006.

(51) Int. Cl.
*A61B 17/70* (2006.01)

(52) U.S. Cl.
USPC ............................................. 606/86 A

(58) Field of Classification Search
USPC ........... 606/246, 279, 301, 305, 308, 319, 80, 606/86 R, 90, 96, 99, 104, 105, 86 A, 191; 604/104
See application file for complete search history.

(56) References Cited

U.S. PATENT DOCUMENTS

| 5,643,273 | A * | 7/1997 | Clark ........................ 606/96 |
| 6,221,082 | B1 | 4/2001 | Marino et al. |
| 6,485,518 | B1 | 11/2002 | Cornwall et al. |
| 6,540,747 | B1 | 4/2003 | Marino |
| 6,562,046 | B2 | 5/2003 | Sasso |
| 7,306,603 | B2 * | 12/2007 | Boehm et al. .............. 606/279 |
| 2002/0161446 | A1 | 10/2002 | Bryan et al. |
| 2005/0216026 | A1 | 9/2005 | Culbert |
| 2006/0030872 | A1 | 2/2006 | Culbert et al. |
| 2006/0085010 | A1 | 4/2006 | Lieberman |
| 2006/0184177 | A1 | 8/2006 | Echeverri |
| 2008/0119862 | A1 * | 5/2008 | Wicker et al. .............. 606/99 |

* cited by examiner

*Primary Examiner* — Pedro Philogene
*Assistant Examiner* — David Comstock
(74) *Attorney, Agent, or Firm* — AKC Patents; Aliki K. Collins

(57) ABSTRACT

A system for attaching first and second spine fixation elements at a predetermined angle relative to each other to first and second locations of a vertebra, respectively includes first and second guide arms pivotally connected to each other at a first pivot point and configured to pivot around a pivot axis passing through the first pivot point, and first and second guide tubes passing through first and second elongated through-bore openings formed in the first and second guide arms, respectively, and forming an X-structure as they exit the first and second through-bore openings.

24 Claims, 31 Drawing Sheets

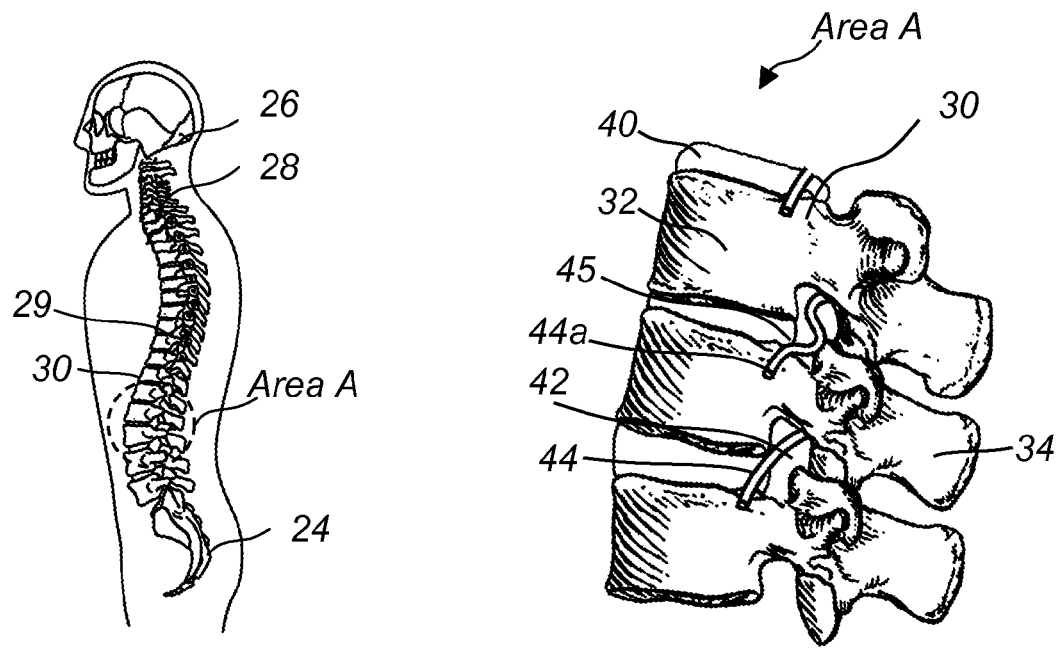
FIG. 1A
FIG. 1B
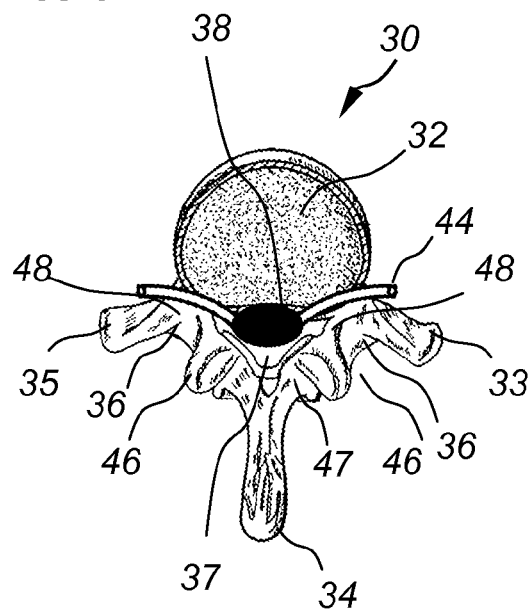
FIG. 1C

GUIDANCE SYSTEM, TOOLS AND DEVICES FOR SPINAL FIXATION

CROSS REFERENCE TO RELATED CO-PENDING APPLICATIONS

This application claims the benefit of U.S. provisional application Ser. No. 60/870,251 filed Dec. 15, 2006 and entitled "GUIDANCE SYSTEM, TOOLS AND DEVICES FOR SPINAL FIXATION", the contents of which are expressly incorporated herein by reference.

This application is also a continuation in part of U.S. application Ser. No. 11/779526 filed on Jul. 18, 2007 and entitled "SYSTEM AND METHOD FOR SPINE FIXATION" the contents of which are expressly incorporated herein by reference.

FIELD OF THE INVENTION

The present invention relates to a system and method for spinal fixation, and in particular to a guidance system, insertion tools and devices for spinal fixation.

BACKGROUND OF THE INVENTION

The human spine comprises individual vertebras 30 (segments) that are connected to each other to form a spinal column 29, shown in FIG. 1. Referring to FIGS. 1B and 1C, each vertebra 30 has a cylindrical bony body (vertebral body) 32, three winglike projections (two transverse processes 33, 35 and one spinous process 34), left and right facet joints 46, lamina 47, left and right pedicles 48 and a bony arch (neural arch) 36. The bodies of the vertebrae 32 are stacked one on top of the other and form the strong but flexible spinal column. The neural arches 36 are positioned so that the space they enclose forms a tube, i.e., the spinal canal 37. The spinal canal 37 houses and protects the spinal cord and other neural elements. A fluid filled protective membrane, the dura 38, covers the contents of the spinal canal. The spinal column is flexible enough to allow the body to twist and bend, but sturdy enough to support and protect the spinal cord and the other neural elements. The vertebras 30 are separated and cushioned by thin pads of tough, resilient fiber known as inter-vertebral discs 40. Disorders of the spine occur when one or more of the individual vertebras 30 and/or the inter-vertebral discs 40 become abnormal either as a result of disease or injury. In these pathologic circumstances, fusion of adjacent vertebral segments may be tried to restore the function of the spine to normal, achieve stability, protect the neural structures, or to relief the patient of discomfort.

Several spinal fixation systems exist for stabilizing the spine so that bony fusion is achieved. The majority of these fixation systems utilize fixation elements such as rods wires or plates that attach to screws threaded into the vertebral bodies, facets or the pedicles. Because the outer surface of the vertebral body is typically non-planar and the structure of the vertebras is relatively complex, it is important that the fixation elements (e.g., rods, plates, wires, staples and/or screws) are properly aligned when they are inserted into the vertebras. Improper alignment may result in improper or unstable placement of the fixation element and/or disengagement of the fixation element. However, achieving and maintaining accurate positioning and guidance of these fixation elements has proven to be quite difficult in practice. Such positioning difficulties are further complicated by the fact that the alignment angle for a fixation device through one vertebral body or pair of vertebral bodies will be unique to that individual due to individual differences in the spinal curvature and anatomies.

Accordingly, there is a need for a guidance system and tools for accurate placement of spinal fixation elements.

SUMMARY OF THE INVENTION

The present invention relates to a system and method for spinal fixation, and in particular to a guidance system, insertion tools and devices for spinal fixation.

In general, in one aspect, the invention features an angular guidance system used to attach first and second spine fixation elements at a predetermined angle relative to each other to first and second locations of a vertebra, respectively. The angular guidance system includes first and second guide arms pivotally connected to each other at a first pivot point and configured to pivot around a pivot axis passing through the first pivot point, and first and second guide tubes passing through first and second elongated through-bore openings formed in the first and second guide arms, respectively, and forming an X-structure as they exit the first and second through-bore openings.

Implementations of this aspect of the invention may include one or more of the following features. The system further includes first and second guide wires configured to be inserted through the first and second guide tubes into the first and second vertebral locations. The pivot axis is perpendicular to a plane defined by the first and second guide arms. The system may further include a goniometer disposed between the first and second guide arms for measuring and setting the predetermined angle. The system may further include a deployable vertical indicator indicating a direction vertical to a spinal midline. The system may further include a Z-wire indicator passing through the first pivot point. The system may further include an elongated threaded bolt connecting the first and second guide arms and allowing them to pivot around the pivot axis in a controlled way and in angular intervals of a tenth of a degree. The elongated threaded bolt passes through first and second posts attached to the back of the first and second guide arms, respectively. The system may further include first and second handles attached to the first and second guide tubes, respectively. The system may further include a cannulated drill configured to be inserted over the first and second guide wires and through the first and second guide tubes for drilling at the first and second vertebral locations. The system may further include a facet access assembly for dilating tissue surrounding the guide wires and inserting first and second cannulas into the first and second vertebral locations, respectively. The facet access assembly comprises a cannula, an obturator, an obturator release trigger and a handle. The obturator passes through the cannula and comprises a guide wire channel for inserting the obturator over the guide wires. Releasing the obturator release trigger advances the obturator forward and causes dilation of the tissue surrounding the guide wires. The obturator is configured to be removed after the tissue dilation leaving behind the cannula. The system may further include a screwdriver configured to place first and second screws to the first and second vertebral locations through the first and second cannulas, respectively. The screwdriver includes a screw retention sleeve, a handle attached to a proximal end of the screw retention sleeve, a screw retention element attached to a distal end of the screw retention sleeve and a screw release/capture trigger. The first and second locations may be a facet joint, pedicle, transverse processes, pars, lamina, vertebral body, sacrum, lateral mass, or occiput locations.

In general in another aspect the invention features a method for attaching first and second spine fixation elements at a predetermined angle relative to each other to first and second locations of a vertebra, respectively. The method includes inserting a first guide wire into the first location of the vertebra and then inserting a first guide arm of an angular guidance system over the first guide wire. The angular guidance system comprises the first guide arm and a second guide arm pivotally connected to the first guide arm and configured to be set at a predetermined angle relative to the first guide arm. Next, setting the second guide arm at the predetermined angle relative to the first guide arm and then inserting a second guide wire through the second guide arm into the second location of the vertebra. Next, dilating tissue around the first guide wire and inserting and attaching the first fixation element into the first location of the vertebra and then dilating tissue around the second guide wire and inserting and attaching the second fixation element into the second vertebra location.

Among the advantages of this invention may be one or more of the following. The system allows the fixation elements to be implanted and removed one piece at a time via minimally invasive surgery. The angular positioning of the fixation elements relative to each other reduces the need for repeated fluoroscopy imaging which reduces the surgery time and the radiation exposure of the patient.

BRIEF DESCRIPTION OF THE DRAWINGS

Referring to the figures, wherein like numerals represent like parts throughout the several views:

FIG. 1A is a side view of the human spinal column;
FIG. 1B is an enlarged view of area A of FIG. 1A;
FIG. 1C is an axial cross-sectional view of a lumbar vertebra.

DETAILED DESCRIPTION OF THE INVENTION

The present invention relates to a system and a method for spinal fixation, and in particular, to a guidance system, insertion tools and devices for spinal fixation.

Figure 2A:
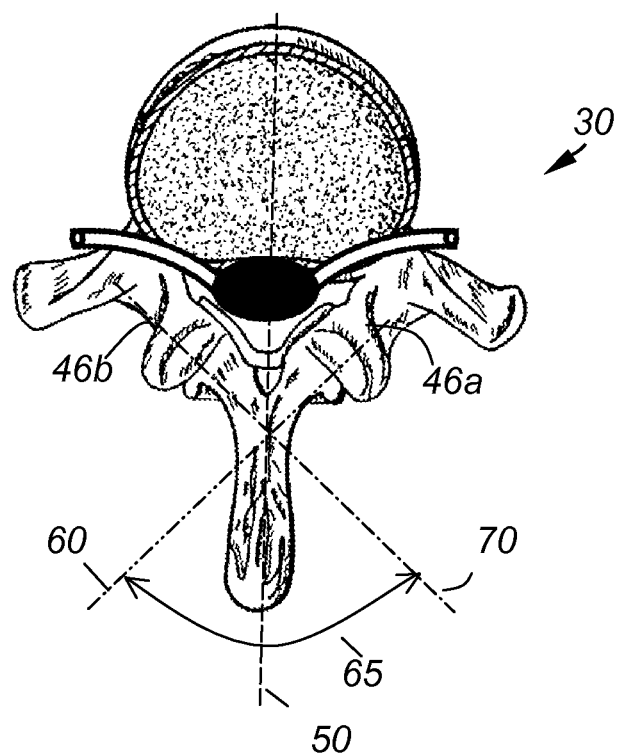
FIG. 2A illustrates placement directions of two facet screws for securing two facet joints.
Figure 2B:
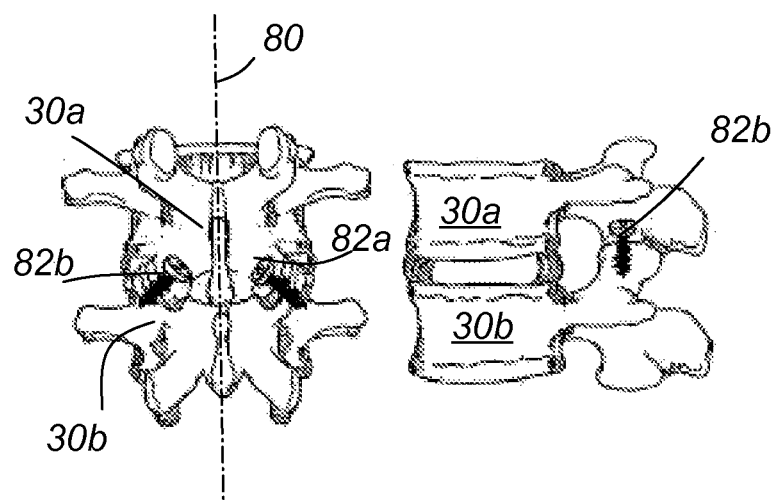
FIG. 2B illustrates two facet screws mounted on two adjacent vertebras bilaterally symmetrically to the spinal midline 80.

Referring to FIG. 2A, 2B, spinal fixation elements 82a, 82b are used to secure together first and second facet joints 46a, 46b. The spinal fixation elements 82a, 82b are inserted along the directions 60, 70, respectively. Directions 60, 70 form an angle 65 between them. In most cases, directions 60, 70 are symmetrically positioned to the left and right of the spinal midline 80 which is perpendicular to the dichotome 50 of angle 65. In this example, fixation elements 82a, 82b are facet screws and are placed in a trans-facet way for connecting adjacent vertebras 30a, 30b. In other examples, fixation elements 82a, 82b, may be staples, wires, or pins, and they may connect adjacent or non-adjacent vertebras via trans-facet, trans-laminar, trans-facet-pedicular, trans-pedicular, or through any other vertebral location.

A minimally invasive procedure of attaching spinal fixation elements 82a, 82b, includes the steps of inserting guide wires in the locations of the facet joints 46a, 46b along the directions 60, 70, respectively, dilating the tissue areas surrounding the facet wires, inserting a cannula around each guide wire, drilling or tapping the bone locations where the screws are inserted and finally inserting the screws though the cannulas and attaching them to the facet joints.

Guide wires or Kirschner wires (also called a K-wires) are thin, rigid wires that can be used to stabilize bone fragments in orthopedics and other types of medical and veterinary surgery. Kirschner wires were introduced in surgical procedures by Martin Kirschner in 1909. They are sterilized, sharpened, smooth stainless steel pins and have different sizes. These wires can be drilled through the bone to hold bone fragments in place. They are placed percutaneously (through the skin), thus avoiding an operation in some cases. In other cases, the K-wires are used after an operation to hold bone fragments in place. In some cases the K-wires include threads for threading into the bone. Typically K-wires are placed under fluoroscopic observation. However, fluoroscopy increases the surgery time and exposes the patient to radiation. The present invention utilizes a guidance system for inserting K-wires that minimizes the use of fluoroscopy and decreases the surgery set-up time.

Figure 3:
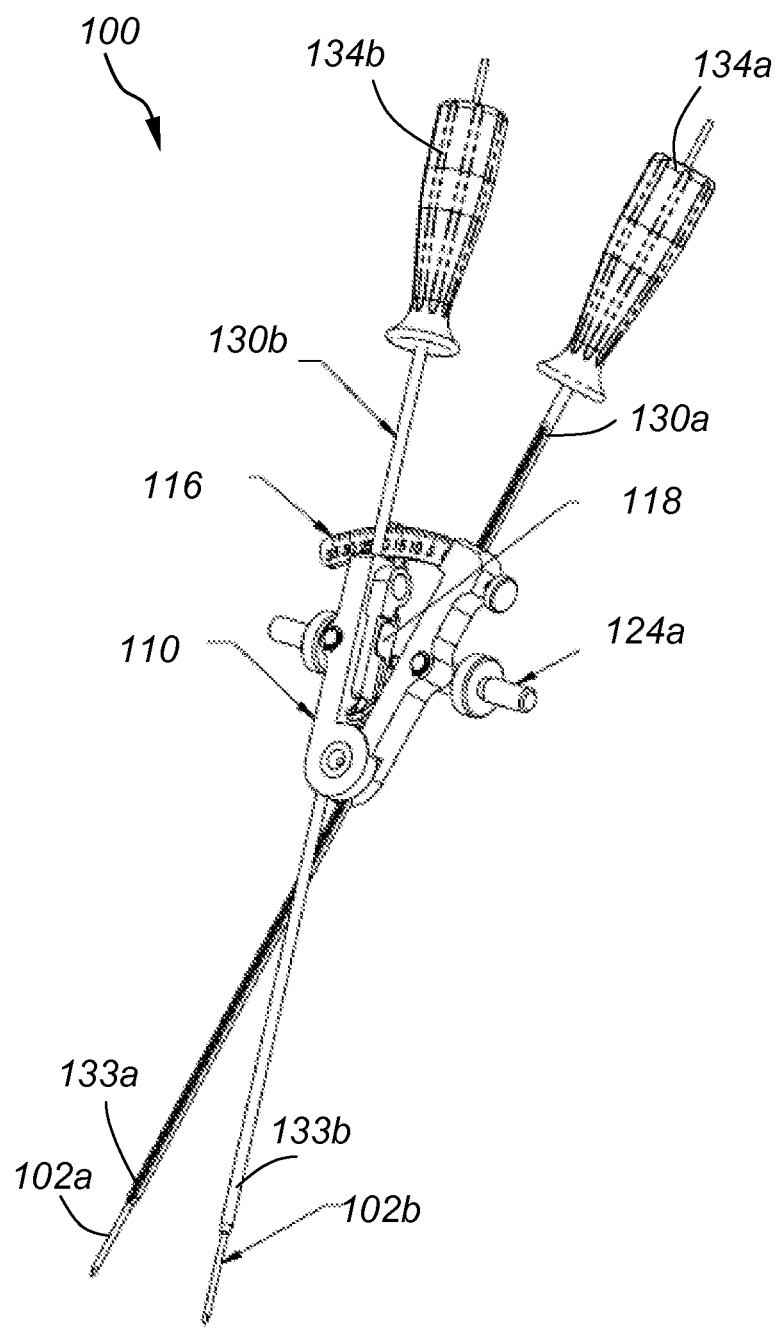
FIG. 3 is a front perspective view of an X-guide positioning system according to this invention.
Figure 4:
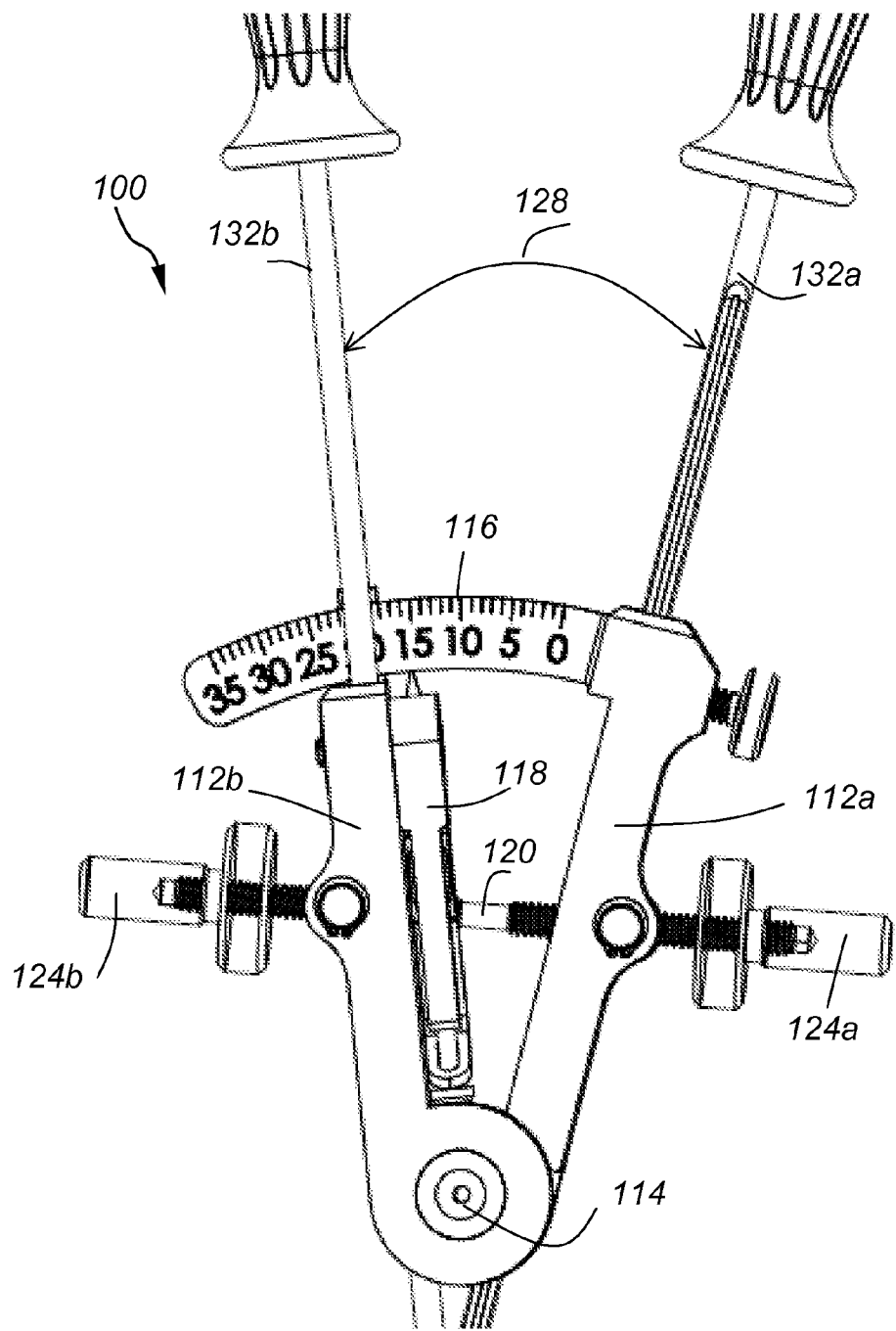
FIG. 4 is a detailed front view of the X-guide's goniometer.
Figure 8:
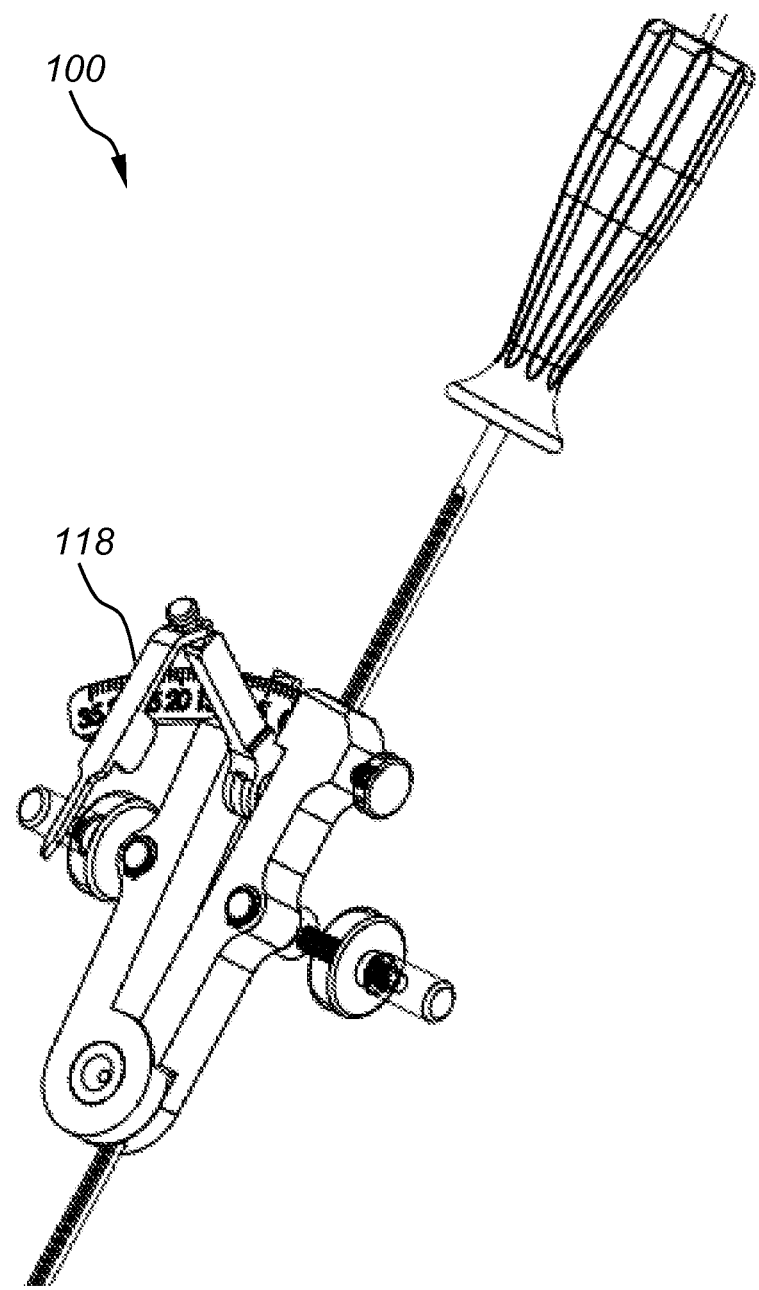
FIG. 8 illustrates deploying the vertical indicator of the X-guide system.
Figure 15:
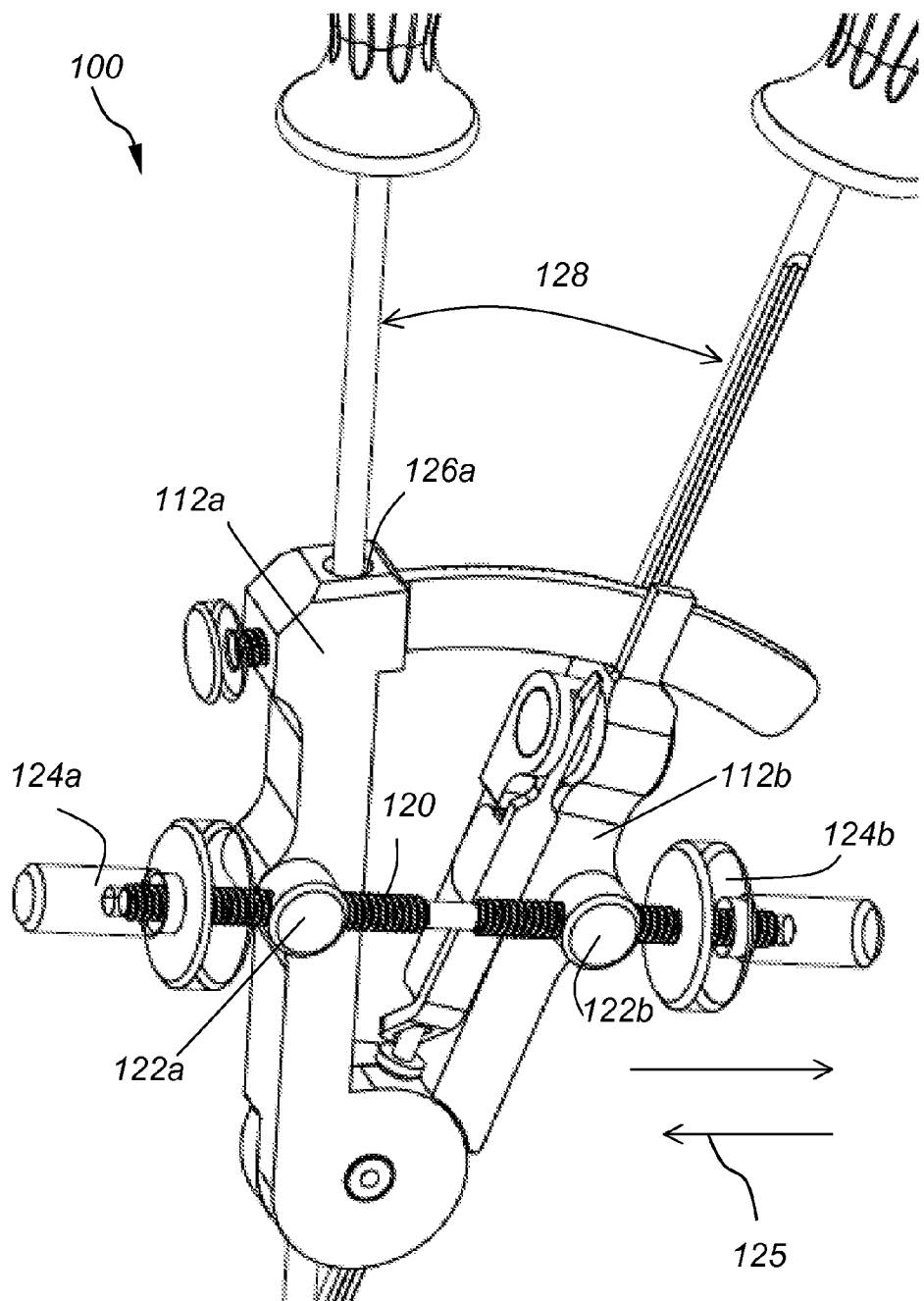
FIG. 15 is a back view of the X-guide system of FIG. 3
Figure 16A:
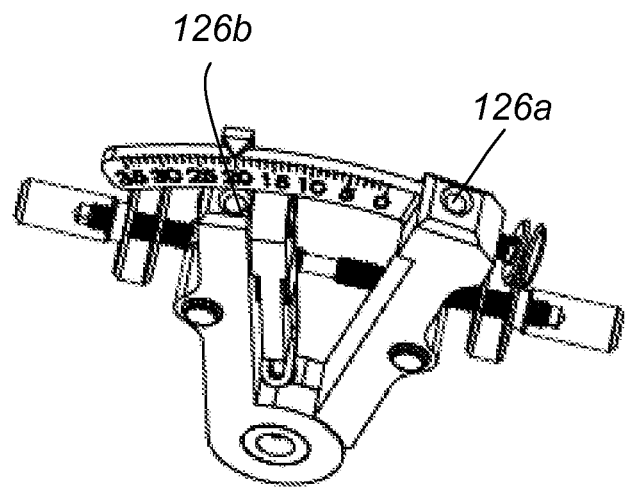
FIG. 16A is a top view of the X-guide system of FIG. 3.
Figure 16B:
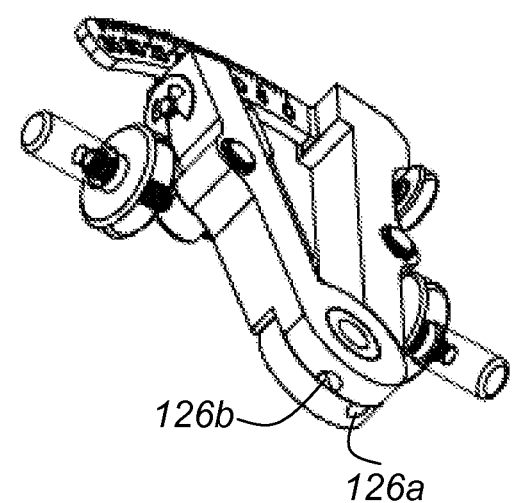
FIG. 16B is a bottom view of the X-guide system of FIG. 3.
Figure 17:
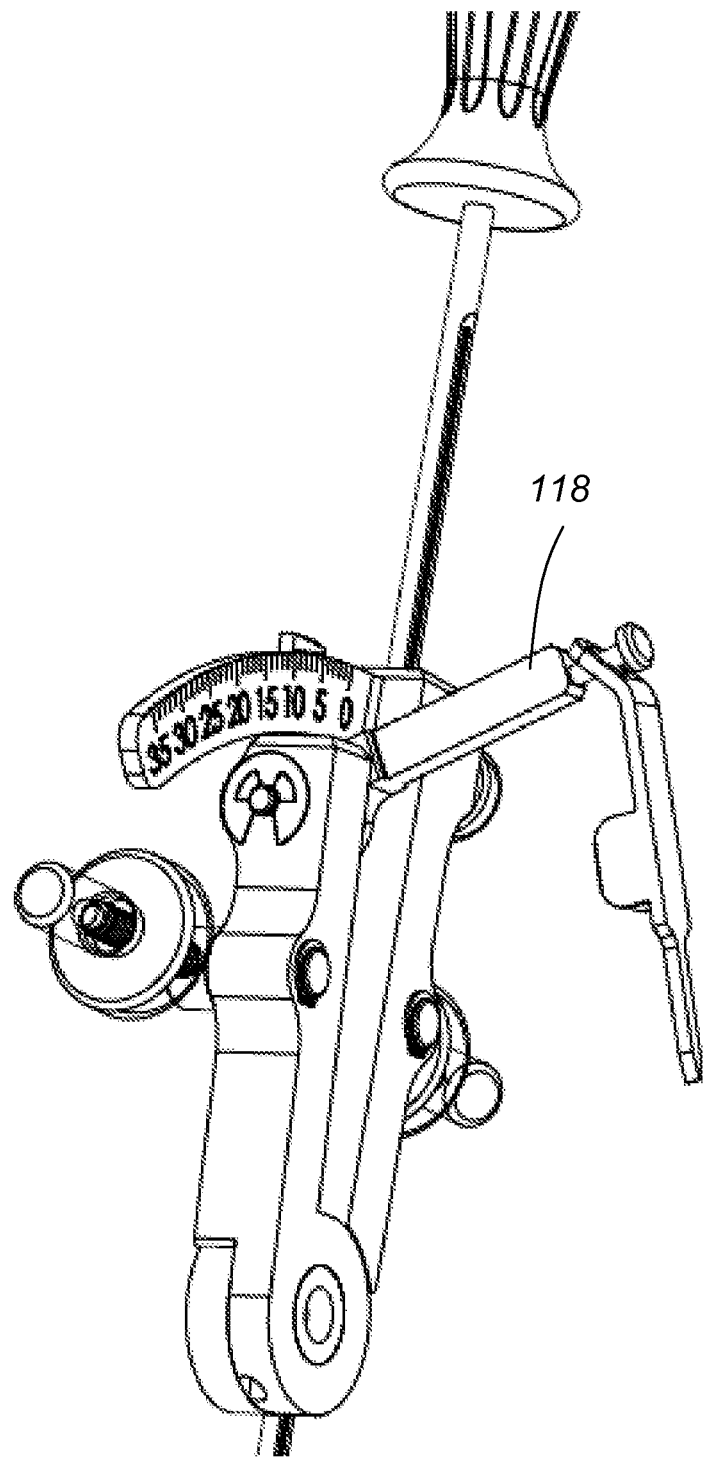
FIG. 17 is a side perspective view of the X-guide system of FIG. 3.
Figure 18:
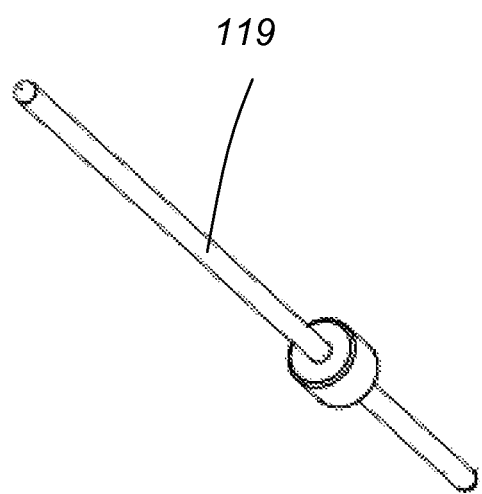
FIG. 18 is a perspective view of the z-wire.

Referring to FIG. 3, and FIG. 4, an X-guide system 100 for inserting guide wires 102a, 102b into a patient's spinal locations includes an X-guide assembly 110, and first and second guide tubes assemblies 130a, 130b. X-guide assembly 110 includes first and second arms 112a, 112b that pivot around axis 113, shown in FIG. 5. Pivot axis 113 is perpendicular to the plane defined by the to arms 112a, 112b and passes through pivot point 114. First and second arms 112a, 112b are attached to each other at the pivot point 114. The X-guide assembly also includes a goniometer 116 disposed between the two pivoting arms 112a, 112b for measuring the angle 128 between the two arms. The X-guide assembly also includes a deployable vertical indicator 118 for indicating a direction vertical to the spinal midline 80. Vertical indicator 118 is shown in FIG. 4 in the closed position and in FIG. 8 in the open position as it is deployed for measuring the angle between the first arm 112a and the vertical direction to the midline 80. A Z-wire indicator 119 passes through the pivot point 114 and is also used for alignment purposes, shown in FIG. 12. A long threaded bolt 120 connects the two pivoting arms and allows them to pivot relative to each other and around pivot axis 113 in a controlled way and in angular intervals of a tenth of a degree, as shown in FIG. 15. Bolt 120 passes through two short posts 122a, 122b that are attached at the back of arms 112a, 112b, respectively. Two knobs 124a, 124b are threaded at the right and left ends of bolt 120, respectively, and are used to advance the bolt 120 along the direction 125, thereby opening or closing the angle 126 between the first and second arms 112a, 112b. The guide tube assemblies 130a, 130b include elongated hollow tubes 132a, 132b, having handles 134a, 134b, attached to them. Guide wires 102a, 102b pass through through-bore openings in the handles 134a, 134b and through the elongated hollow tubes 132a, 132b and exit at the distal ends 133a, 133b of the elongated tubes 132a, 132b, respectively. The guide tube assemblies 130a, 130b are inserted and pass through through-bore openings 126a, 126b extending along the entire length of the first and second arms 112a, 112b and cross each other forming an X-structure as they exit the through-bore openings 126a, 126b, shown in FIG. 16A, FIG. 16B.

Figure 5:
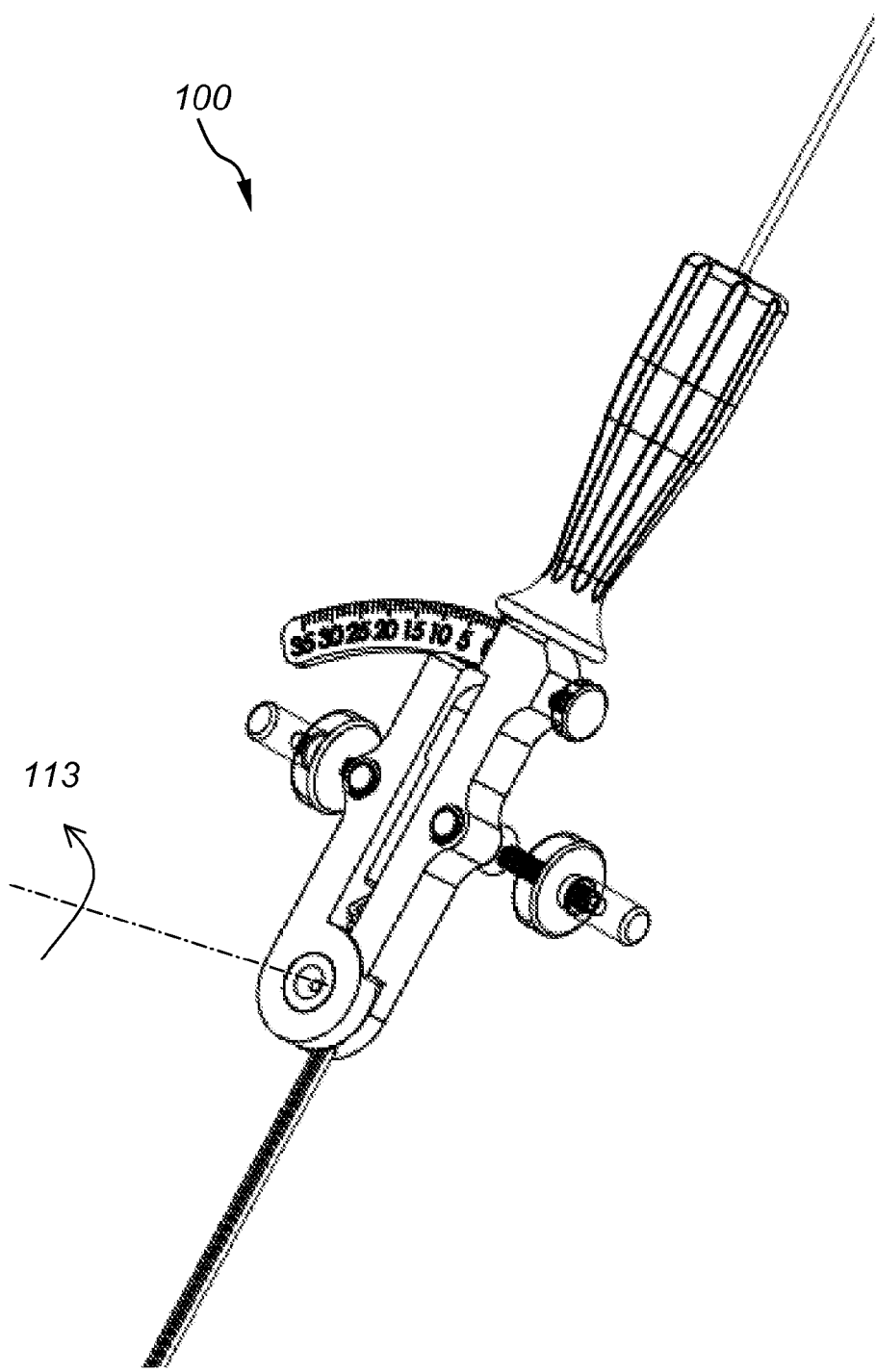
FIG. 5 illustrates the starting position of the X-guide system for inserting a first K-wire in a first facet joint.
Figure 6:
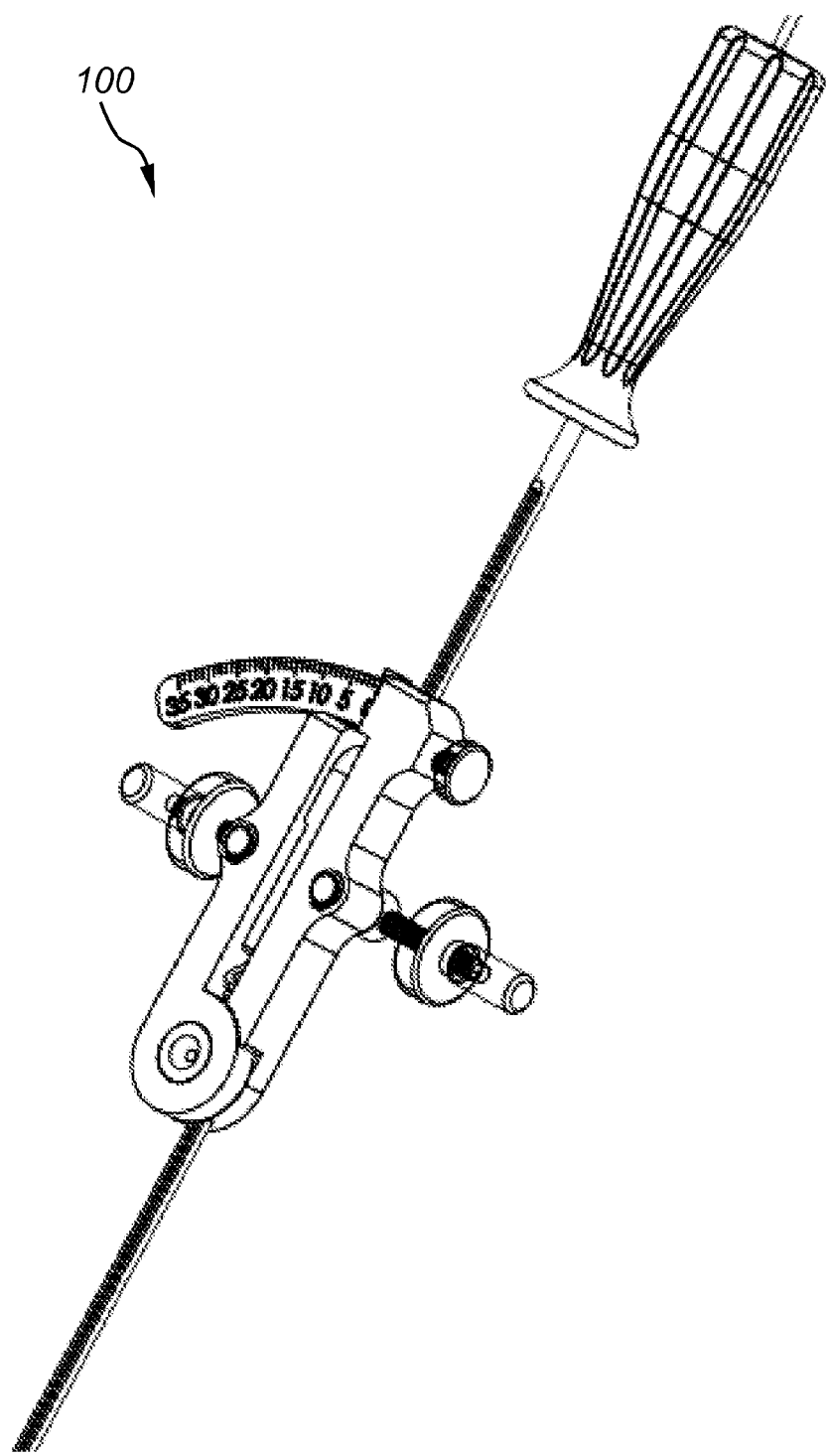
FIG. 6 illustrates lowering the X-guide system for inserting the first K-wire in the first facet joint.
Figure 7:
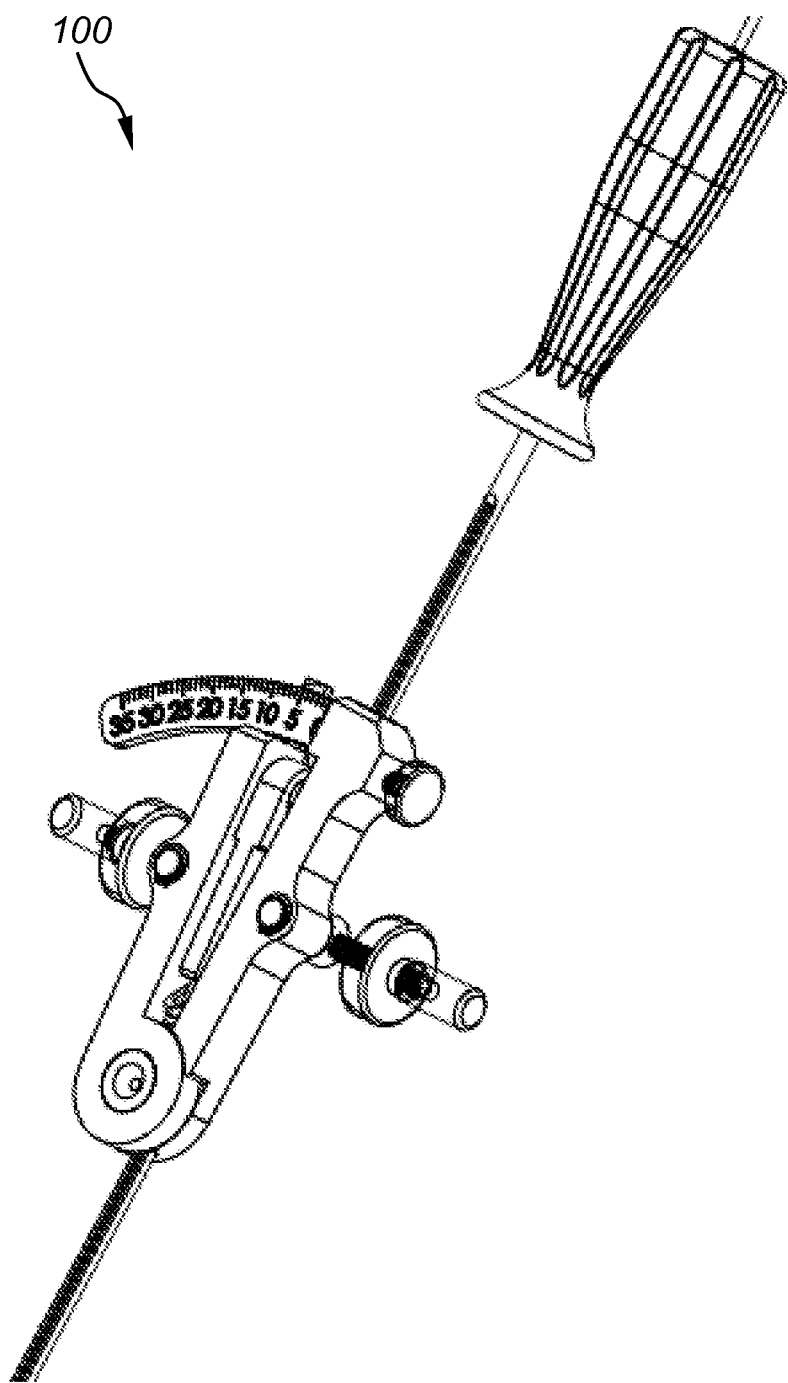
FIG. 7 illustrates opening the X-guide system's arms.
Figure 9:
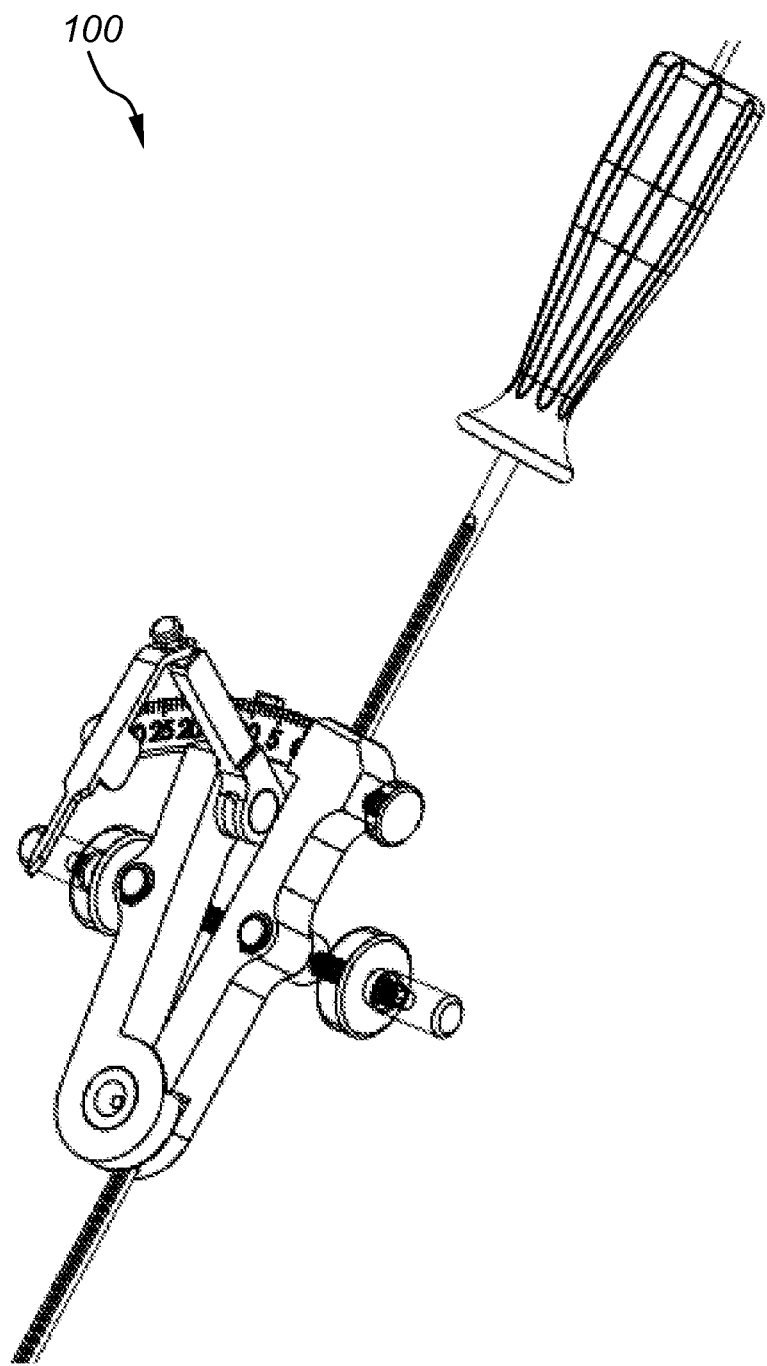
FIG. 9 illustrates finding the vertical direction with the X-guide system.
Figure 10:
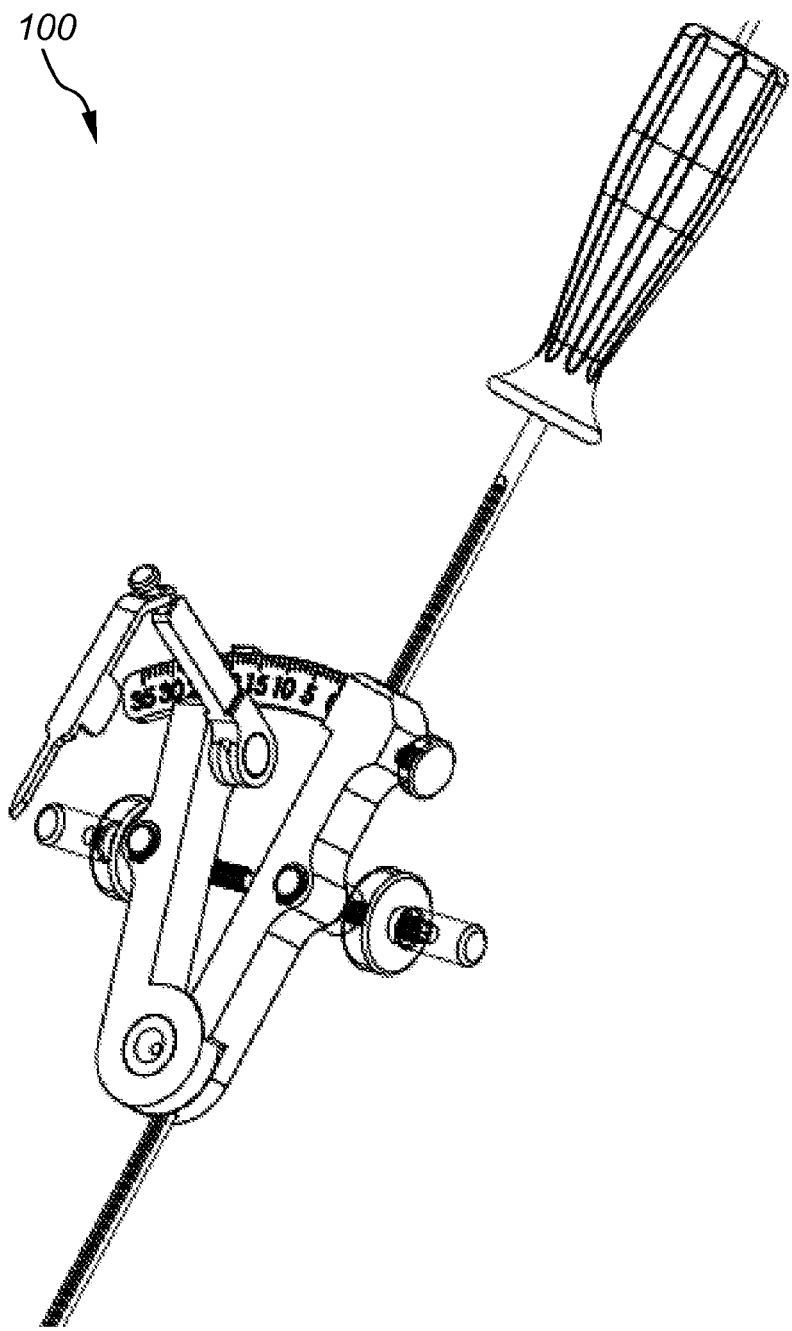
FIG. 10 illustrates doubling the angle between the vertical direction and the first K-wire direction.
Figure 11:
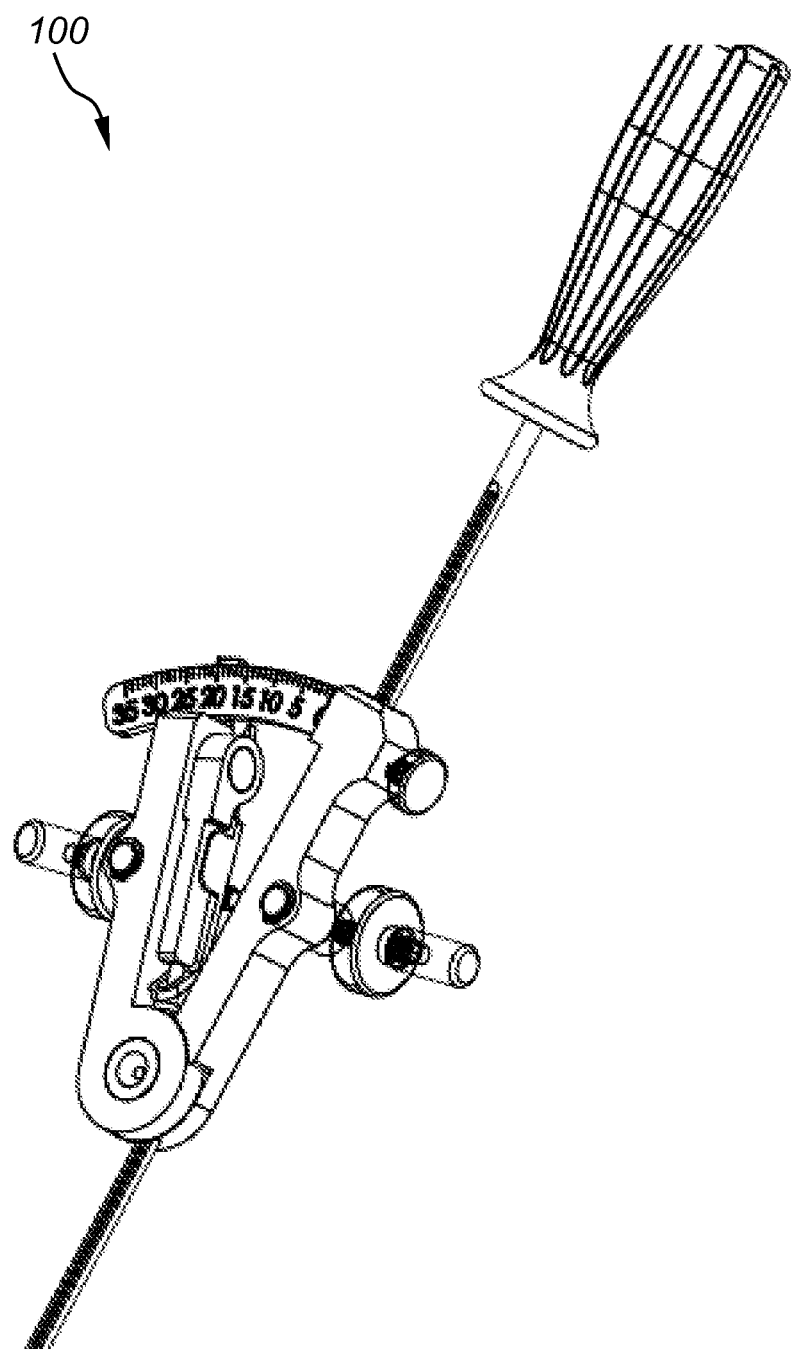
FIG. 11 illustrates stowing the vertical indicator of the X-guide system.
Figure 12:
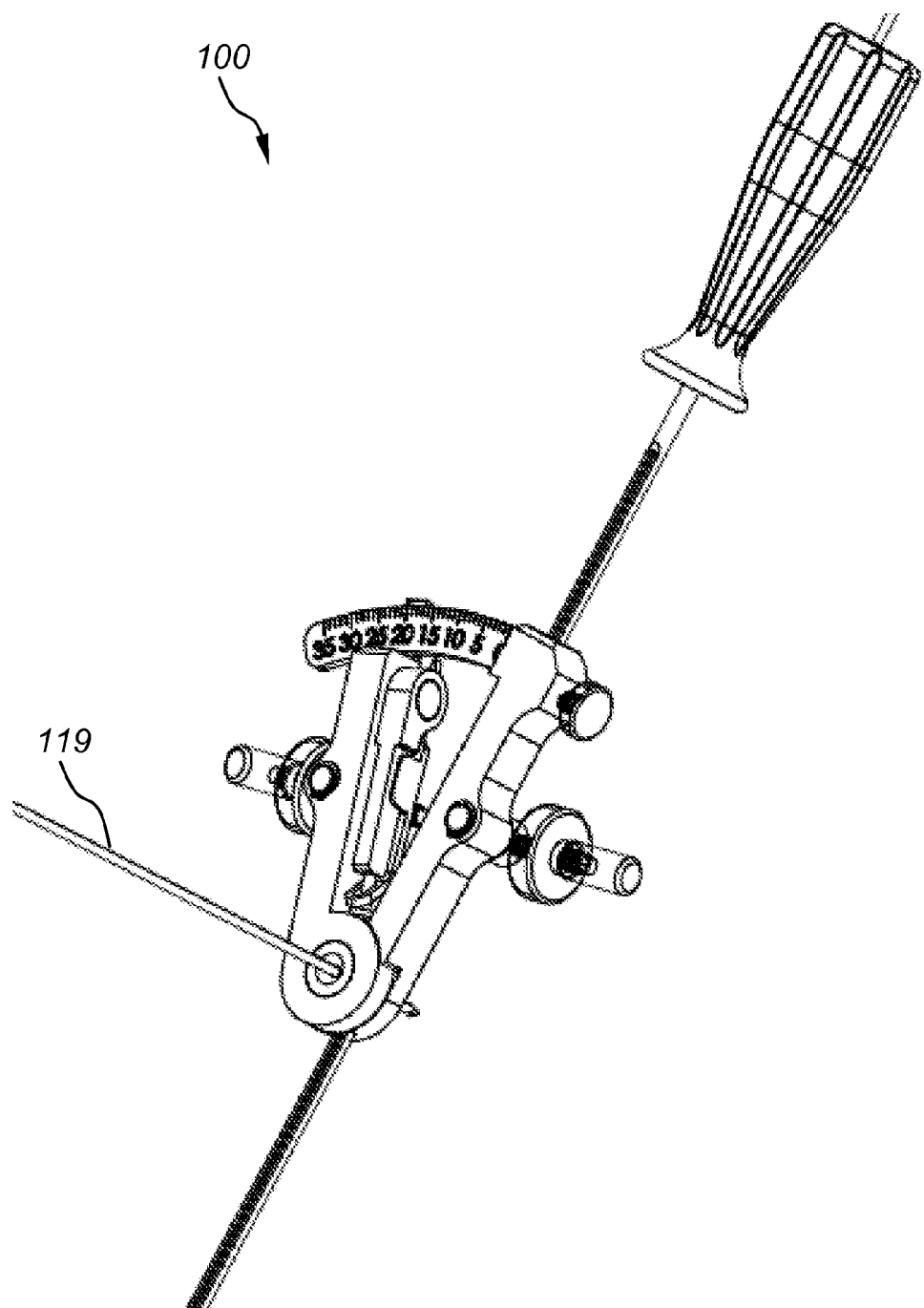
FIG. 12 illustrates utilizing the z-wire to align the X-guide system with the patient's spinal midline.
Figure 13:
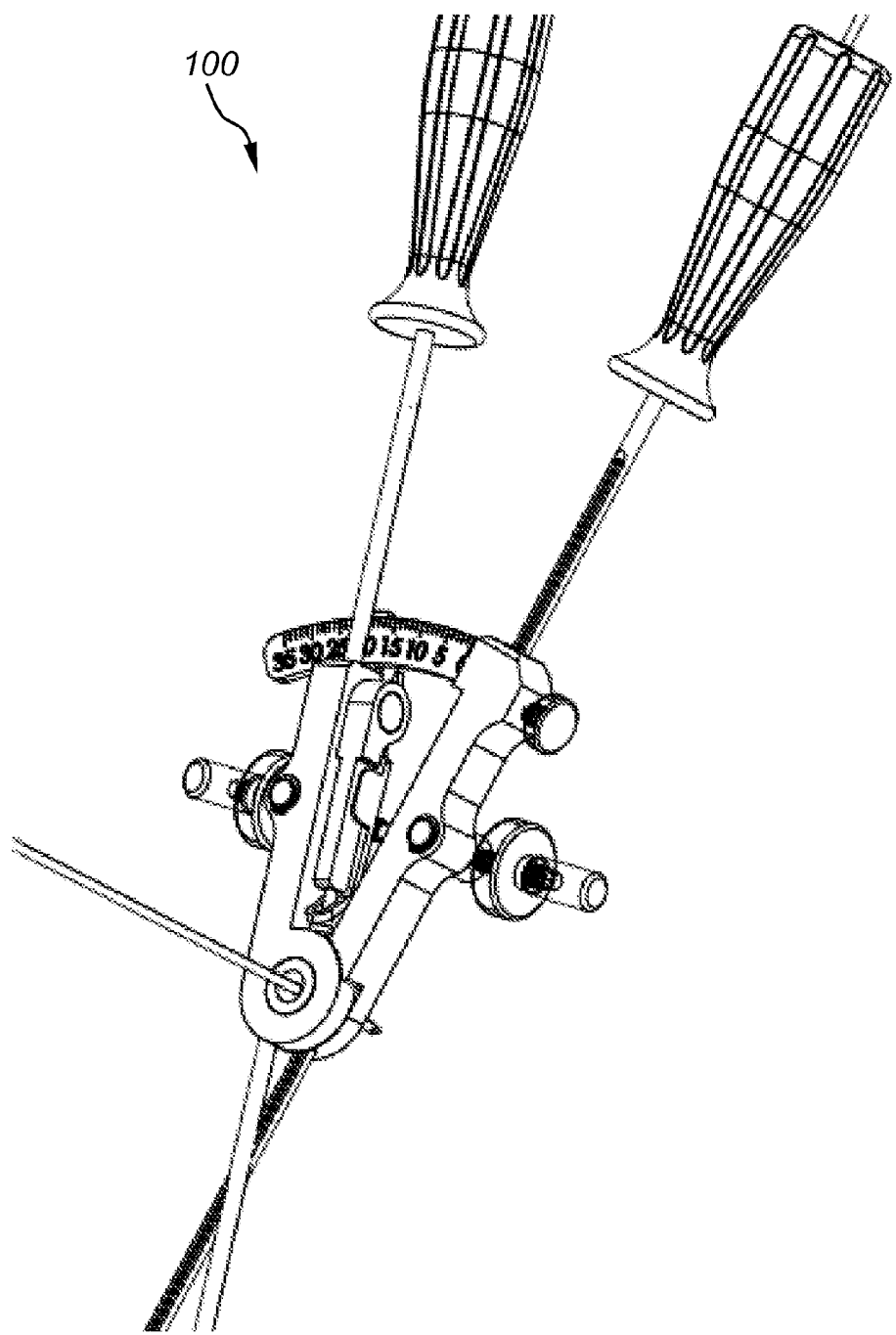
FIG. 13 illustrates inserting a second guide tube in the X-guide system of FIG. 3.
Figure 14:
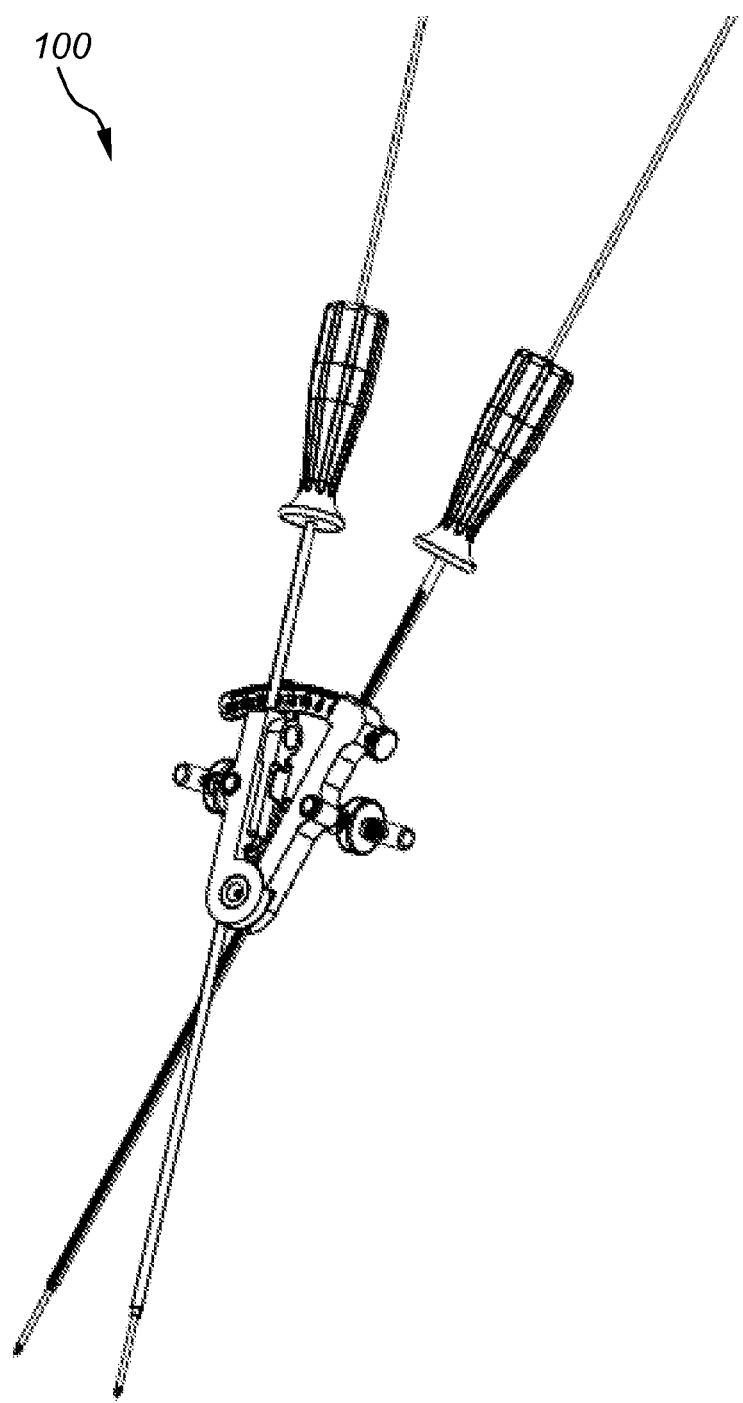
FIG. 14 illustrates inserting a second K-wire in the second guide tube and placing it in a second facet joint.

The process of inserting the guide wires 102a, 102b with the X-guide system of FIG. 3 is described with reference to FIG. 5-FIG. 14. First the first guide tube assembly 130a is inserted through the through-bore opening 126a of the first arm 112a (FIG. 5). Next a first guide wire 102a is inserted through the hollow elongated tube 132a into a first facet joint 46a of the patient's spine under fluoroscopic observation (FIG. 6). Next, the second arm 112b of the X-guide assembly is pivotably opened (FIG. 7) and then the vertical indicator 118 is deployed (FIG. 8) and used to find the direction vertical to the patient's spinal midline 80 (FIG. 9). The angle between the first arm and the vertical direction is measured and then the second arm is pivoted to an angle setting relative to the first arm having a value twice the value of the angle between the first arm and the vertical direction (FIG. 10). This angular positioning of the second arm relative to the first arm is based on the assumption that the two facet joints 46a, 46b are symmetrically disposed relative to the spinal midline 80. In most human anatomies this is a valid assumption and allows the surgeon to place the second guide wire with the help of the X-guide system 100 without he need for a second fluoroscopy. In cases where this assumption is not valid, the angle between the spinal midline and the second facet joint is determined from the first fluoroscopy results and the second arm of the X-guide system is set to the calculated value. Next the vertical indicator is stowed between the two open arms (FIG. 11) and the Z-wire is used to align the X-guide system with the patient's spinal midline 80 (FIG. 12). Once the X-guide system is aligned with the patient's spinal midline the second guide tube 132b is inserted in the through-bore opening 126b of the second arm 112b (FIG. 13) and then the second guide wire 102b is inserted through the tube 132b and into the patient's second facet joint 46b (FIG. 14). Next, the X-guide system 100 is removed leaving behind the correctly placed guide wires 102a, 102b. The X-guide system 100 may be used both in minimally invasive surgeries and open spine surgeries.

Figure 19:
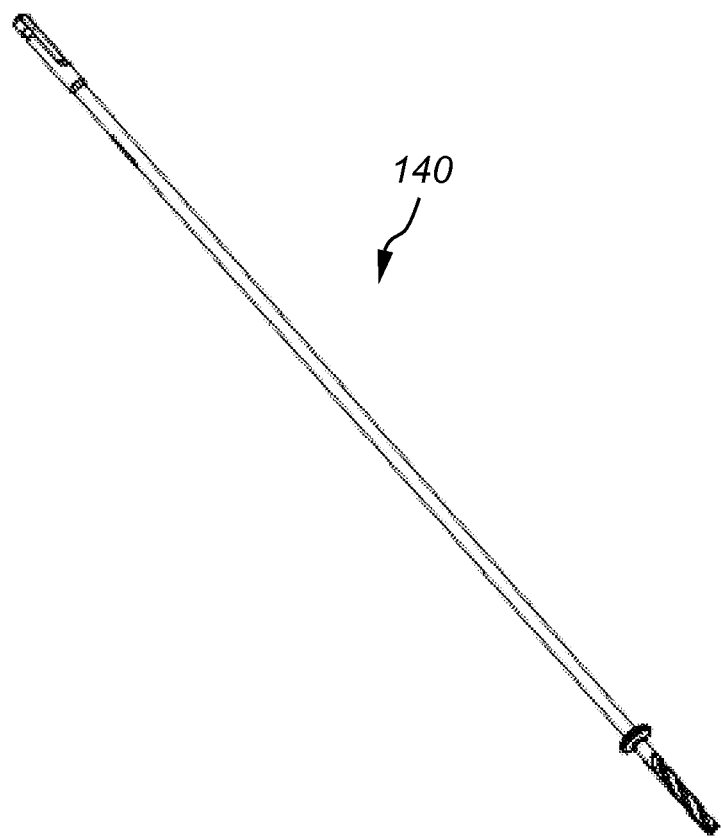
FIG. 19 is a perspective view of a cannulated drill.
Figure 25A:
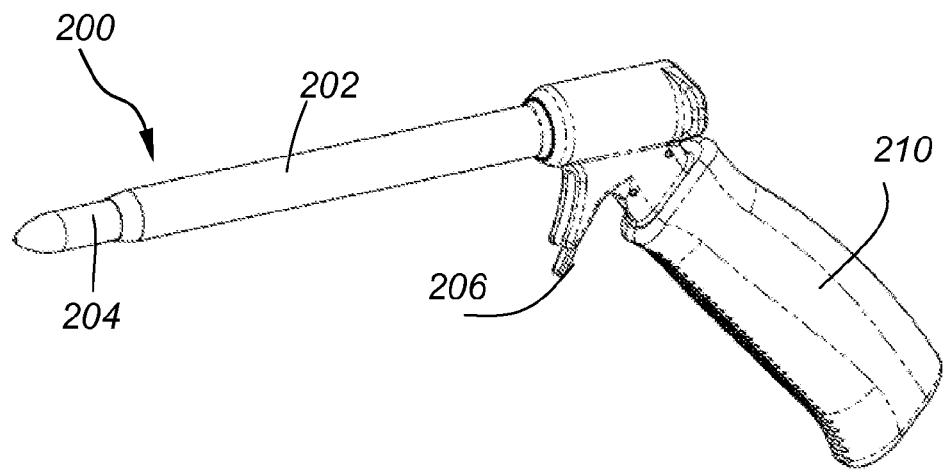
FIG. 25A is a front perspective view of a facet access assembly.
Figure 25B:
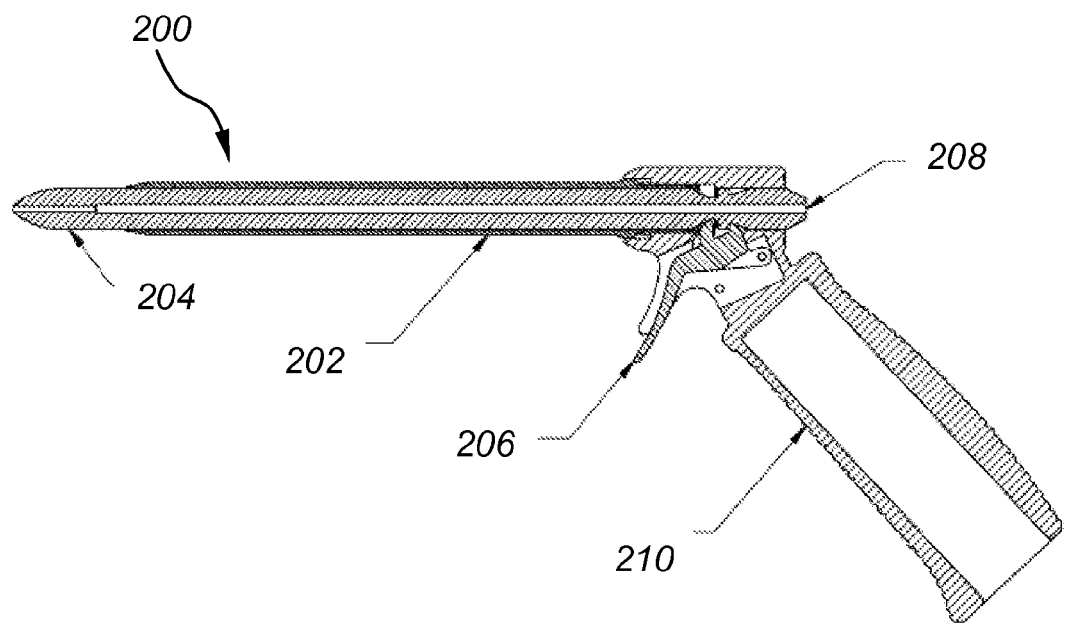
FIG. 25B is a cross-sectional side view of the facet access assembly of FIG. 25A.
Figure 26A:
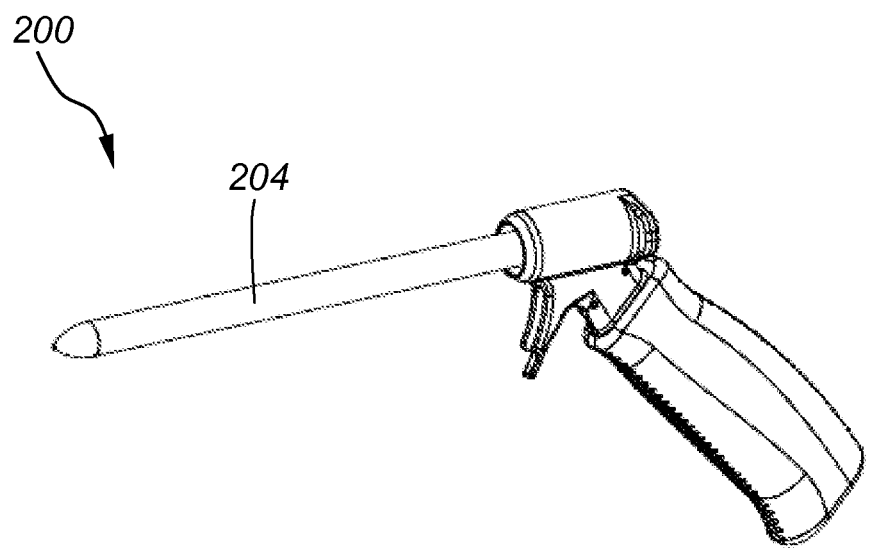
FIG. 26A illustrates inserting an obturator into the handle of the facet access assembly of FIG. 25A.
Figure 26B:
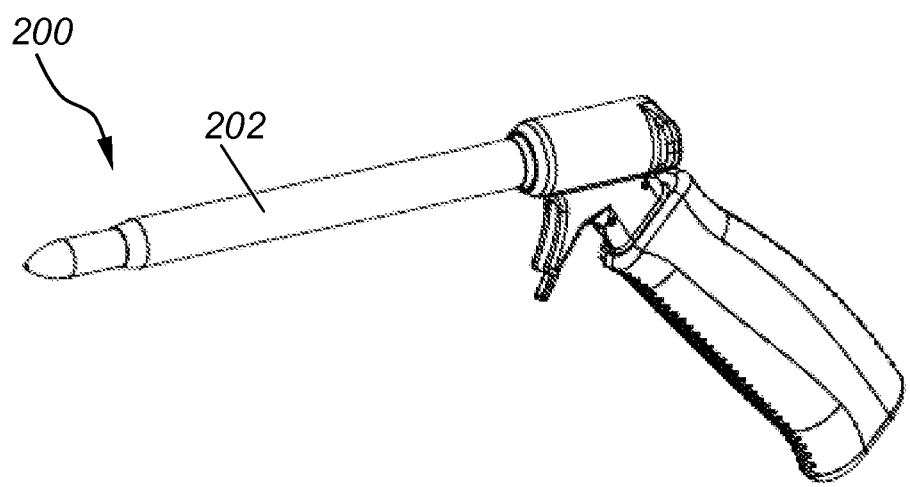
FIG. 26B illustrates inserting a cannula around the obturator and into the handle of the facet access assembly of FIG. 25A.
Figure 27A:
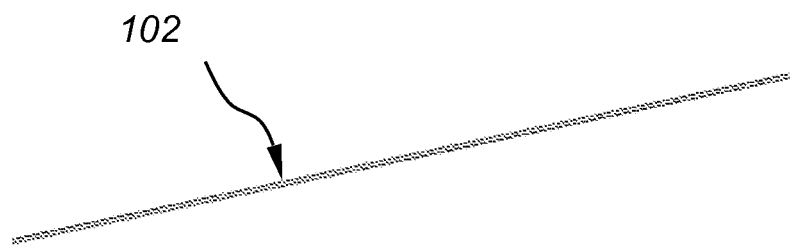
FIG. 27A illustrates inserting a K-wire into the facet access assembly of FIG. 25A.
Figure 27B:
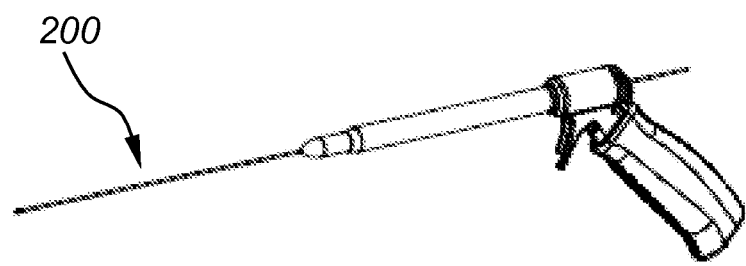
FIG. 27B illustrates driving the cannula of the facet access assembly of FIG. 25A into the bone.
Figure 27C:
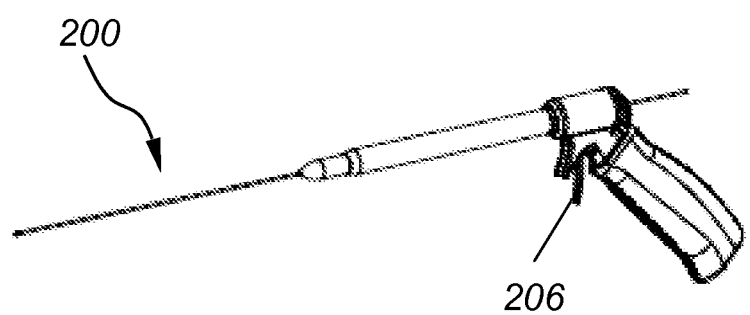
FIG. 27C illustrates pulling the trigger of the facet access assembly of FIG. 25A to release the obturator.
Figure 28A:
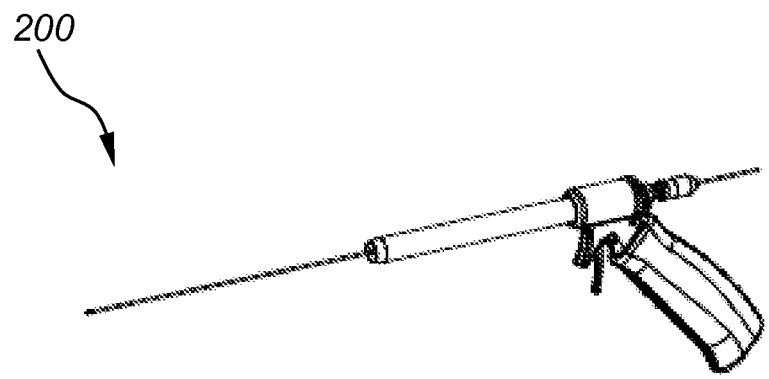
FIG. 28A illustrates fully advancing the cannula of the facet access assembly of FIG. 25A into the bone.
Figure 28B:
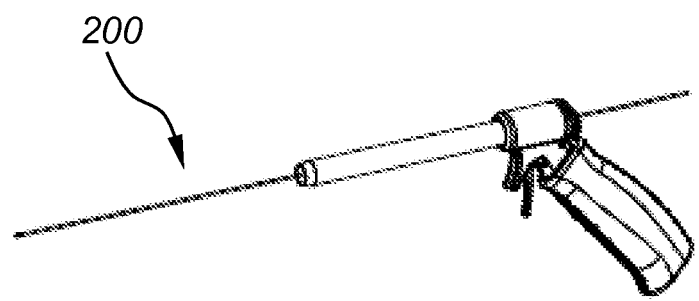
FIG. 28B illustrates removing the obturator of the facet access assembly of FIG. 25A from the bone.

In the next steps of the spinal fixation surgical procedure the bone is drilled in the locations marked with the guide wires, the tissue is dilated around the guide wires and facet screws are inserted through cannulas and screwed into the facet joint locations marked by the guide wires. Referring to FIG. 19 a cannulated drill 140 is inserted over the guide wires 102a, 102b and the bone is drilled in the locations marked by the guide wires. The tissue surrounding the guide wires is dilated with the facet access assembly 200 shown in FIG. 25A and FIG. 25B. The facet access assembly 200 includes a cannula 202, an obturator 204, an obturator release trigger 206 and a handle 210. The obturator passes through the cannula and includes a guide wire channel 208 that allows the obturator to be inserted over the guide wires 102a, 102b. The trigger 206 is used to advance the obturator forward. As the obturator advances forward around the guide wire it pushes and dilates the tissue surrounding the guide wire and opens a channel around the wire for the placement of the cannula 202. FIG. 26A illustrates inserting the obturator 204 into the handle 210 of the facet access assembly 200 and FIG. 26B illustrates inserting the cannula 202 around the obturator 204 and into the handle 210 of the facet access assembly 200. FIG. 27A illustrates a K-wire and FIG. 27B illustrates positioning the facet access assembly 200 over the K-wire and driving the cannula 202 into the bone. FIG. 27C illustrates pulling the trigger 206 of the facet access assembly 200 to release the obturator 204 and to push and dilate the tissue surrounding the K-wire with the obturator. FIG. 28A illustrates fully advancing the cannula of the facet access assembly 200 into the bone through the channel opened by the obturator around the K wire. FIG. 28B illustrates removing the obturator of the facet access assembly 200 from the bone, leaving behind the cannula 202 and the K-wire. Once the cannula 202 is placed in the patient's spinal locations marked with the guide wires, spine fixation tools and devices are inserted through the cannula to the marked locations.

Figure 20:
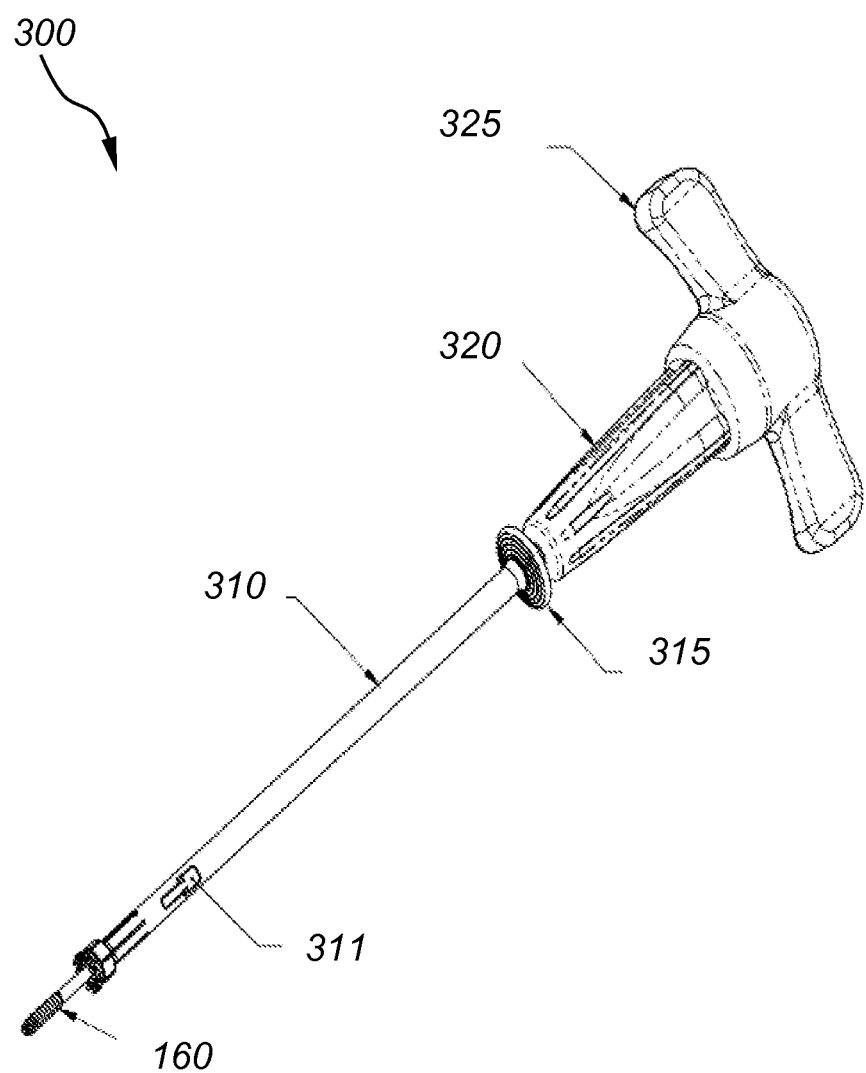
FIG. 20 is a perspective view of a screwdriver assembly with a screw-washer system attached.
Figure 21A:
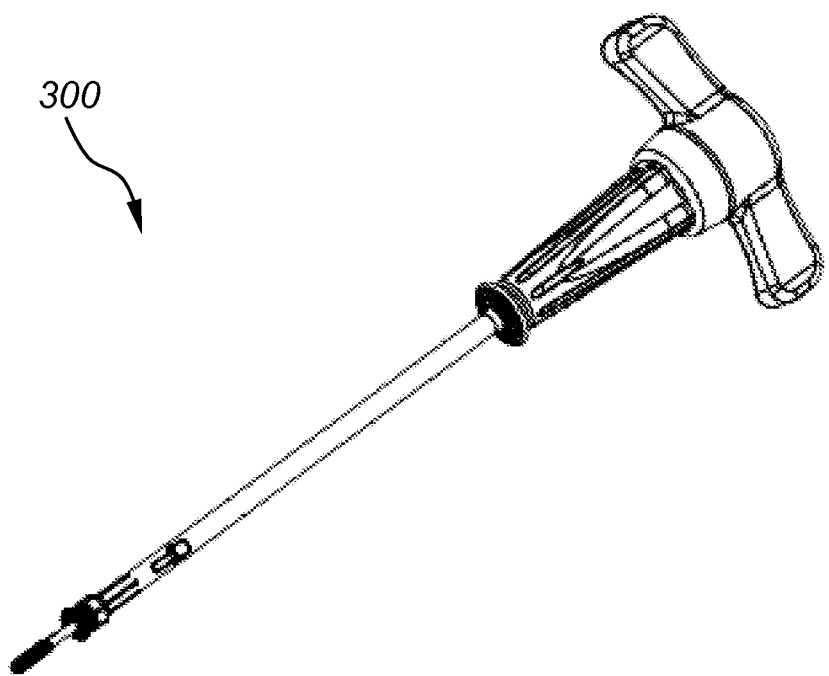
FIG. 21A is a perspective view of the screwdriver assembly of FIG. 20 with the screw-washer system released.
Figure 21B:
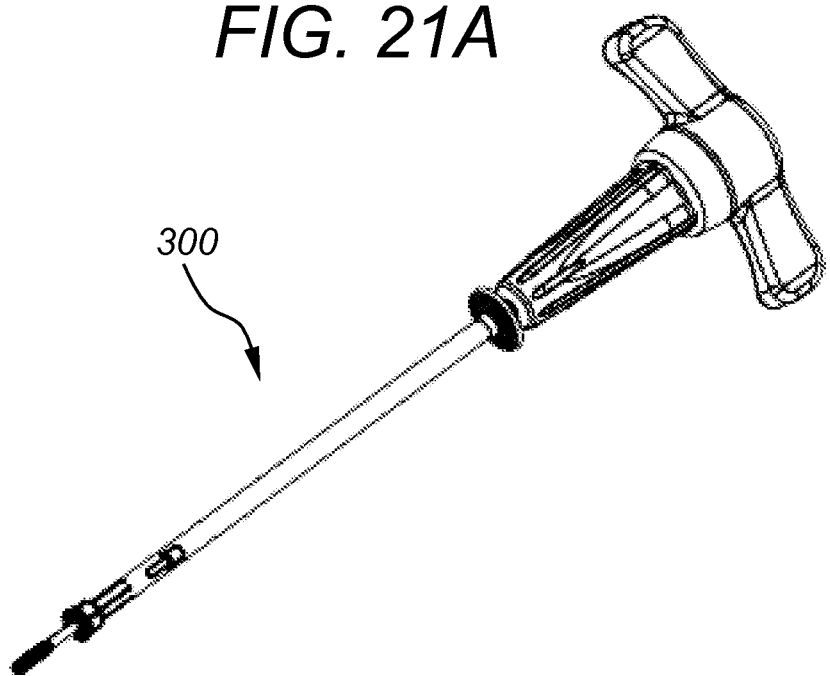
FIG. 21B is a perspective view of the screwdriver assembly of FIG. 20 with the screw-washer system retained.
Figure 22A:
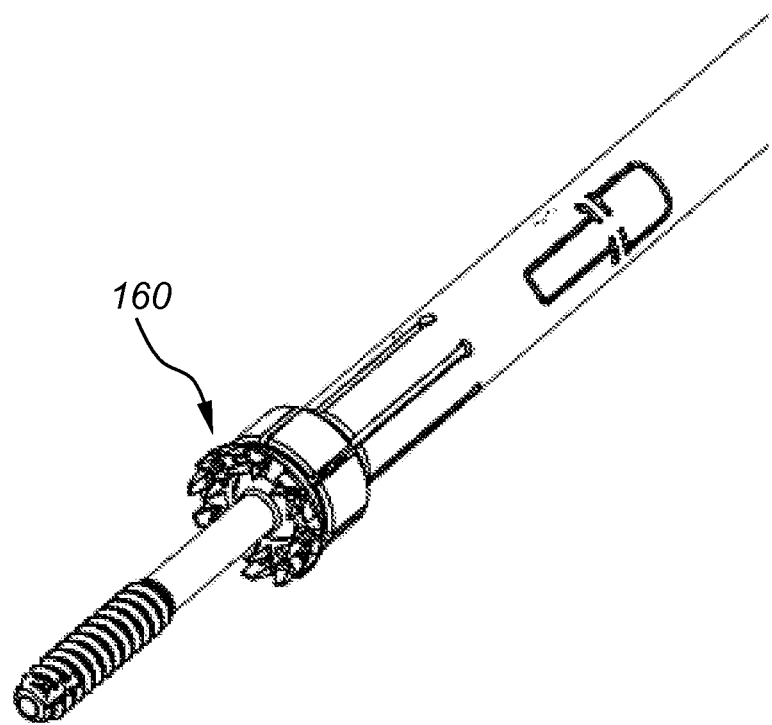
FIG. 22A is a detailed view of the retained screw-washer system of FIG. 21B.
Figure 22B:
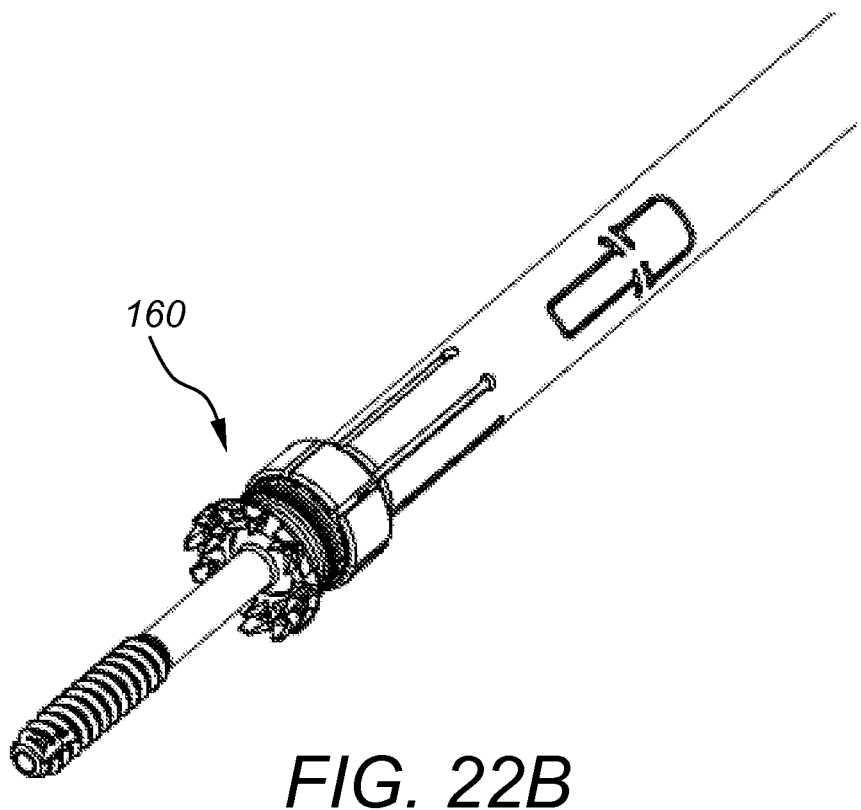
FIG. 22B a detailed view of the released screw-washer system of FIG. 21A.

Referring to FIG. 20, a screwdriver assembly 300 is used to deliver and screw a facet screw assembly 160 into the bone through the cannula 202. The screwdriver assembly 300 includes a screw retention sleeve and a handle 320 attached to the proximal end of the retention sleeve 310. Handle 320 includes a detachable T-shaped component 325 that can be used to provide additional torque for driving the screw assembly 160 into the bone. The screw assembly 160 is attached to the distal end of the retention sleeve 310 and can be released or retained by moving the screw release/capture component 315 up or down, as shown in FIG. 21A and FIG. 21B, respectively. Detailed views of the retained and released screw-washer assembly are shown in FIG. 22A, and FIG. 22B, respectively.

Figure 23A:
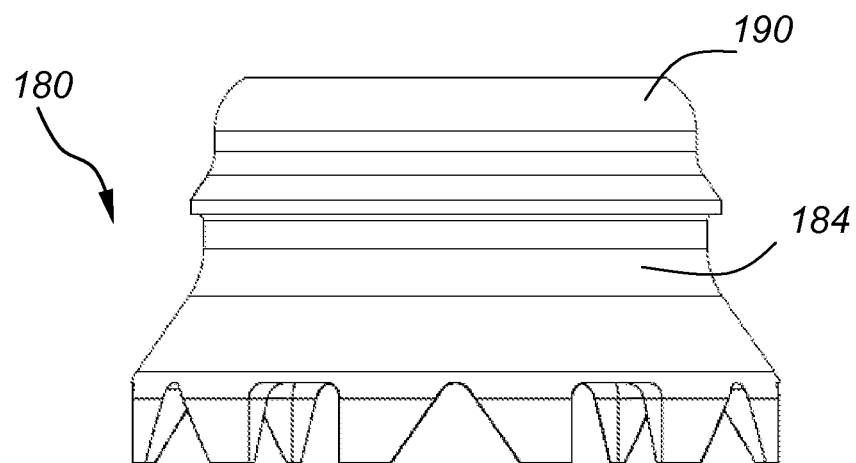
FIG. 23A is a side view of the facet screw washer.
Figure 23B:
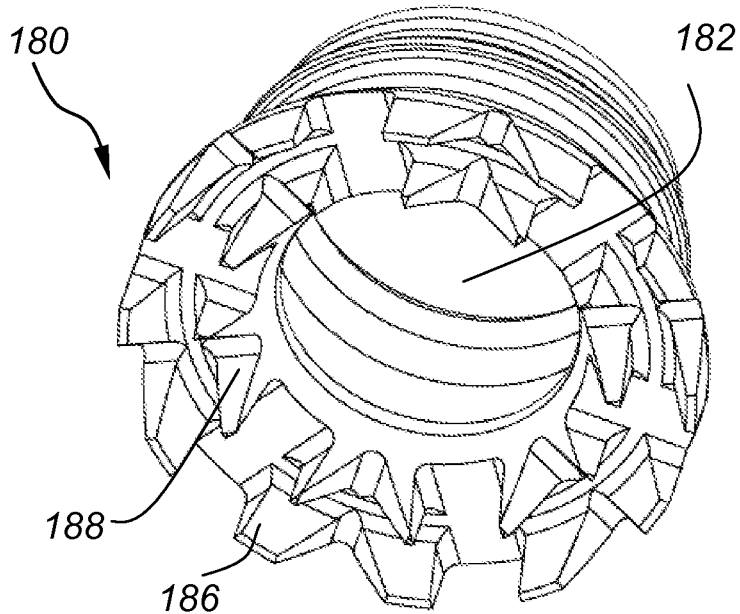
FIG. 23B is a bottom view of the facet screw washer of FIG. 23A.
Figure 24:
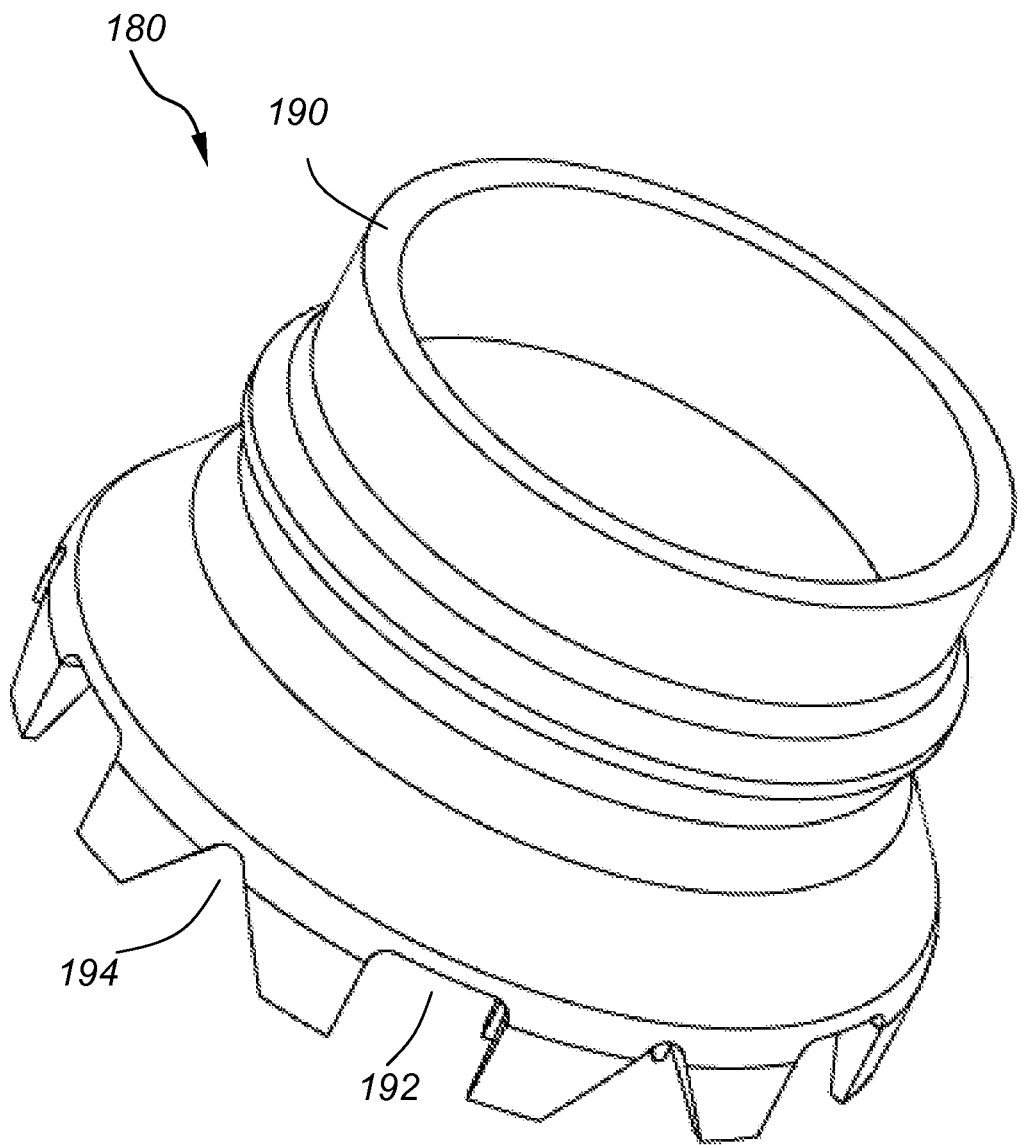
FIG. 24 is a perspective view of the facet screw washer of FIG. 23A before it is formed and attached to the facet screw.
Figure 29:
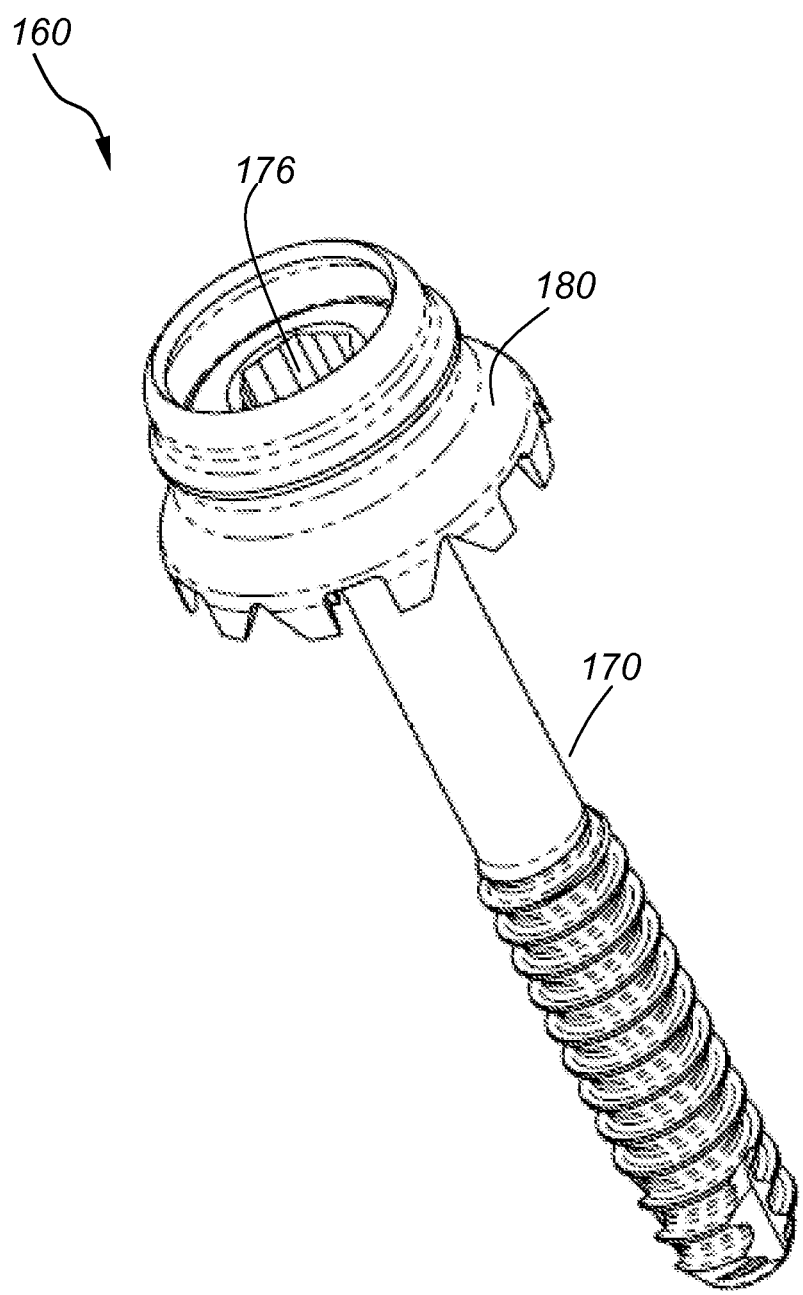
FIG. 29 depicts an embodiment of the polyaxial facet screw and washer system of this invention.
Figure 30:
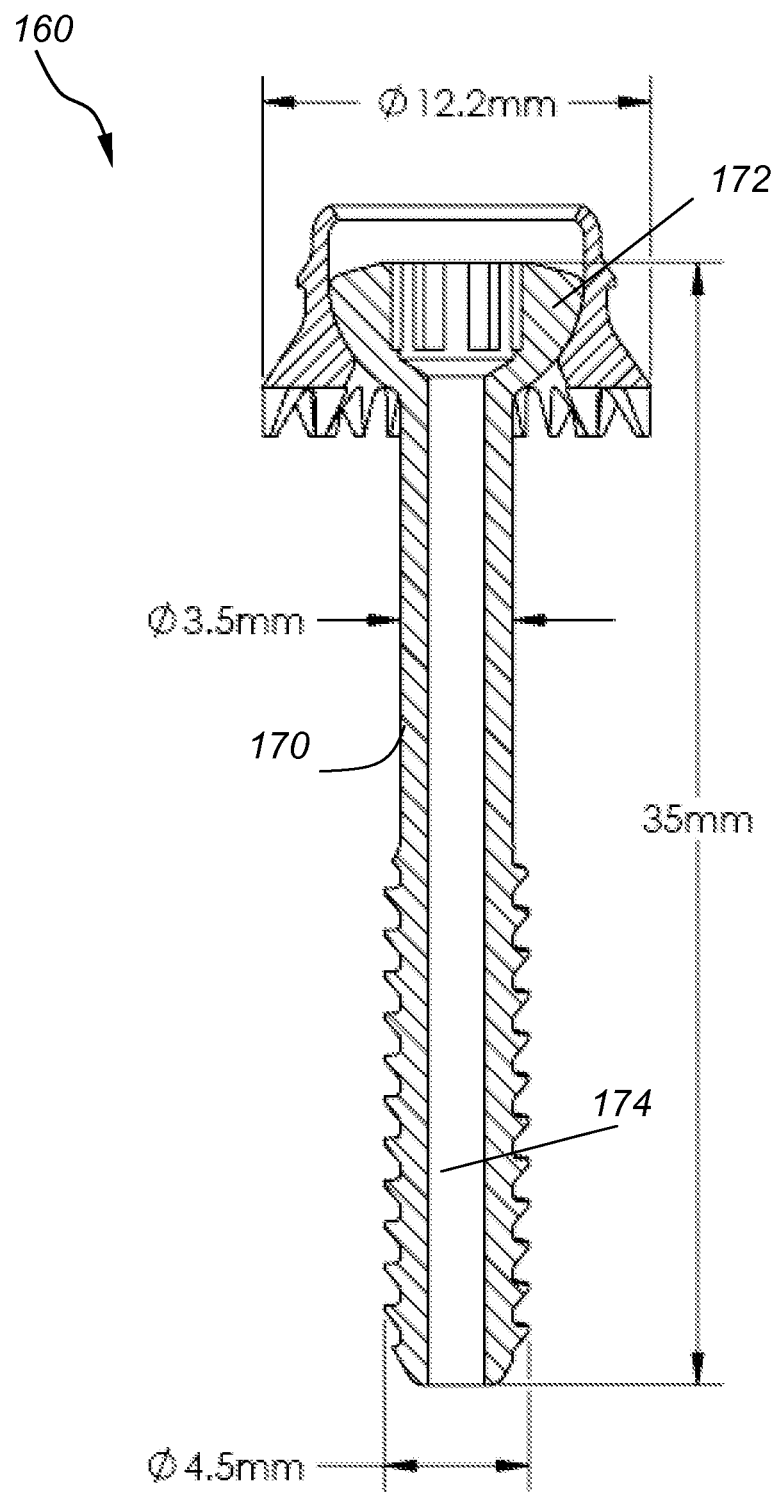
FIG. 30 depicts a cross-sectional side view of the facet screw and washer system of FIG. 29.
Figure 31:
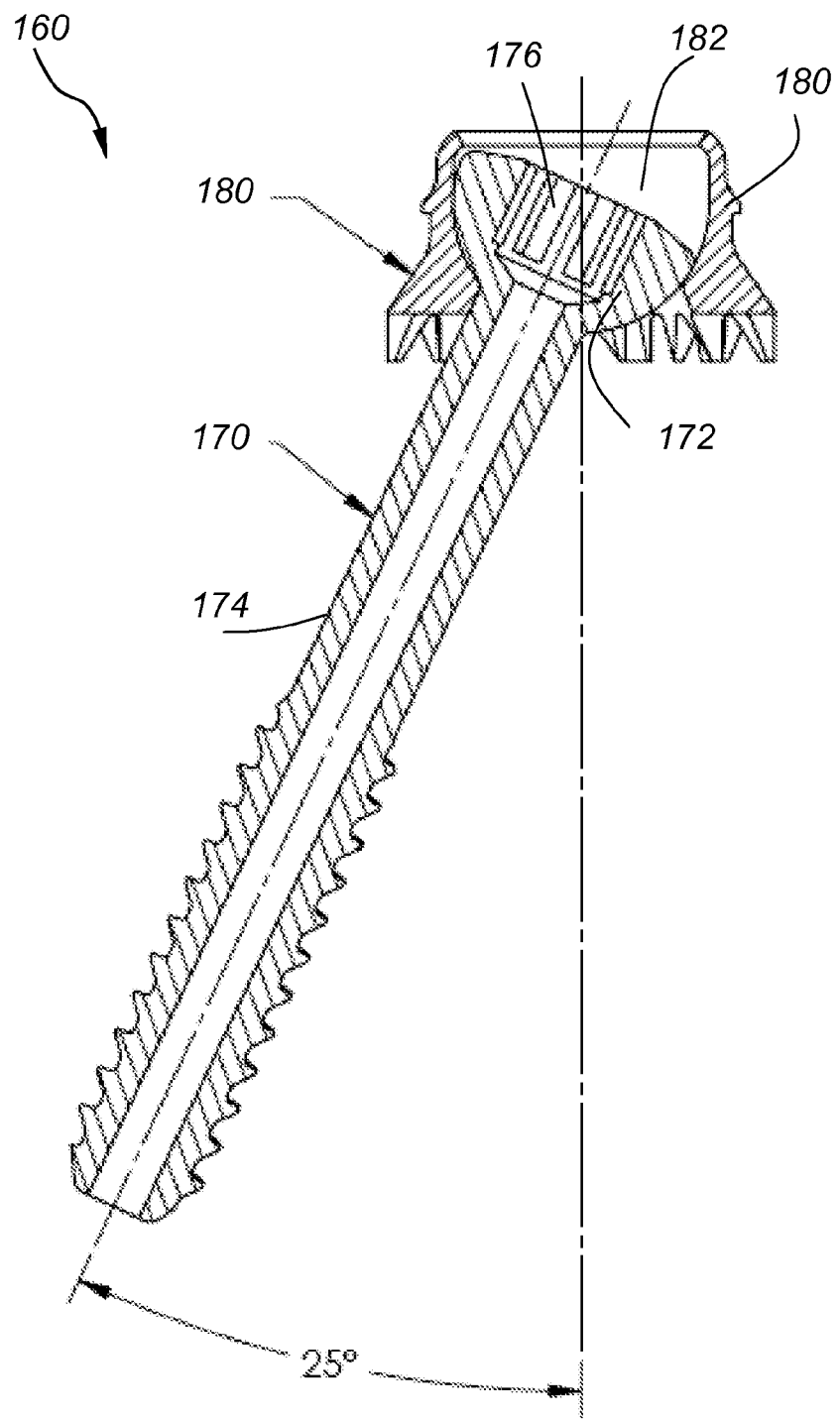
FIG. 31 depicts another cross-sectional side view of the facet screw and washer system of FIG. 29.

Referring to FIG. 29, the facet screw assembly 160 includes a polyaxial screw 170 and a washer 180. Washer 180 is swaged locked on top of the screw head 172. Screw 170 has a cannulated elongated body 174 and a semispherical head 172 that is swaged locked within the opening 182 of the washer 180, as shown in FIG. 30. In one example, screw 170 has a length of 35 mm and a diameter of 4.5 mm. Screw head 172 is polyaxially rotatable within the opening 182 of the washer 180, as shown in FIG. 31, until it is secured into the bone with the screwdriver. The head 172 has a hexagonal opening 176 for receiving a hexagonal screwdriver tip. Referring to FIG. 23A, and FIG. 23B washer 180 has a cylindrical body 184 and two rows of teeth 186, 188 extending from the bottom of the washer body 184. Cylindrical body 184 has a semispherical opening 182 for holding the semispherical screw head 172. The top 190 of the opening 182 is initially straight, as shown in FIG. 24, and is flared inwards after the screw head 172 is placed into the opening to lock the head into the opening and prevent it from moving up, as shown in FIG. 23A and FIG. 30. The bottom of the opening 182 has a diameter smaller that the diameter of the semi-spherical head 172 and larger than the diameter of the unthreaded portion of the elongated screw body 174, thus preventing the head 172 from passing through the opening. Teeth 186 and 188 have alternating rectangular 192 and trigonal 194 cross-sections that allow the washer to penetrate and grab into the bone and to prevent it from rotating once it is engaged into the bone.

Several embodiments of the present invention have been described. Nevertheless, it will be understood that various modifications may be made without departing from the spirit and scope of the invention. Accordingly, other embodiments are within the scope of the following claims.

What is claimed is:

1. An angular guidance system used to attach first and second spine fixation elements at a predetermined angle relative to each other to first and second locations of a vertebra, respectively, comprising:
    first and second guide arms pivotally connected to each other at a first pivot point and configured to pivot around a pivot axis passing through said first pivot point so as to be set at said predetermined angle relative to each other;
    first and second guide tubes passing through first and second elongated through-bore openings formed in said first and second guide arms, respectively, and forming an X-structure as they exit said first and second through-bore openings;
    first and second guide wires configured to be inserted through said first and second guide tube into said first and second vertebral locations;
    a facet access assembly for dilating tissue surrounding said guide wires and inserting first and second cannulas into said first and second vertebral locations, respectively; and
    wherein said facet access assembly comprises a cannula, an obturator, an obturator release trigger and a handle and wherein said obturator passes through said cannula and comprises a guide wire channel for inserting the obturator over said guide wires and wherein releasing said obturator release trigger advances said obturator forward and causes dilation of tissue surrounding said guide wires.

2. The system of claim 1 wherein said pivot axis is perpendicular to a plane defined by said first and second guide arms.

3. The system of claim 1 further comprising a goniometer disposed between said first and second guide arms for measuring and setting said predetermined angle.

4. The system of claim 1 further comprising a deployable vertical indicator indicating a direction vertical to a spinal midline.

5. The system of claim 1 further comprising a Z-wire indicator passing through said first pivot point.

6. The system of claim 1 further comprising an elongated threaded bolt connecting said first and second guide arms and allowing them to pivot around said pivot axis in a controlled way and in angular intervals of a tenth of a degree.

7. The system of claim 6 wherein said elongated threaded bolt passes through first and second posts attached to the back of said first and second guide arms, respectively.

8. The system of claim 1 further comprising first and second handles attached to said first and second guide tubes, respectively.

9. The system of claim 1, further comprising a cannulated drill configured to be inserted over said first and second guide wires and through said first and second guide tubes for drilling at said first and second vertebral locations.

10. The system of claim 1 wherein said obturator is configured to be removed after said tissue dilation leaving behind said cannula.

11. The system of claim 1 further comprising a screwdriver configured to place first and second screws to said first and second vertebral locations through said first and second cannulas, respectively.

12. The system of claim 11 wherein said screwdriver comprises a screw retention sleeve, a handle attached to a proximal end of said screw retention sleeve, a screw retention element attached to a distal end of said screw retention sleeve and a screw release/capture trigger.

13. A method for attaching first and second spine fixation elements at a predetermined angle relative to each other to first and second locations of a vertebra, respectively, comprising:
    inserting a first guide wire into said first location of said vertebra;
    inserting a first guide arm of an angular guidance system over said first guide wire wherein said angular guidance system comprises said first guide arm and a second guide arm pivotally connected to said first guide arm and configured to be set at a predetermined angle relative to said first guide arm;
    setting said second guide arm at said predetermined angle relative to said first guide arm;
    inserting a second guide wire through said second guide arm into said second location of said vertebra;
    providing a facet access assembly for dilating tissue surrounding said guide wires and inserting first and second cannulas into said first and second vertebral locations, respectively;
    dilating tissue around said first guide wire and inserting and attaching said first fixation element into said first location of said vertebra;

dilating tissue around said second guide wire and inserting and attaching said second fixation element into said second vertebra location; and wherein said facet access assembly comprises a cannula, an obturator, an obturator release trigger and a handle and wherein said obturator passes through said cannula and comprises a guide wire channel for inserting the obturator over said guide wires and wherein releasing said obturator release trigger advances said obturator forward and causes dilation of the tissue surrounding said guide wires.

14. The method of claim 13 wherein said first and second locations comprise one of facet joint, pedicle, transverse processes, pars, lamina, vertebral body, sacrum, lateral mass, or occiput locations.

15. The method of claim 13 wherein said angular guidance system further comprises first and second guide tubes passing through first and second elongated through-bore openings formed in said first and second guide arms, respectively, and forming an X-structure as they exit said first and second through-bore openings.

16. The method of claim 15 wherein said second guide arm is pivotally connected to said first guide arm at a first pivot point and is configured to pivot around a pivot axis passing through said first pivot point and said pivot axis is perpendicular to a plane defined by said first and second guide arms.

17. The method of claim 16 wherein said angular guidance system further comprises an elongated threaded bolt connecting said first and second guide arms and allowing them to pivot around said pivot axis in a controlled way and in angular intervals of a tenth of a degree.

18. The method of claim 15 wherein said angular guidance system further comprises a goniometer disposed between said first and second guide arms for measuring and setting said predetermined angle.

19. The method of claim 15 wherein said angular guidance system further comprises a deployable vertical indicator indicating a direction vertical to a spinal midline.

20. The method of claim 15 wherein said angular guidance system further comprises a Z-wire indicator passing through said first pivot point.

21. The method of claim 15 further comprising drilling into said first and second locations prior to said inserting and attaching of said first and second fixation elements and wherein said drilling is provided by a cannulated drill configured to be inserted over said first and second guide wires and through said first and second guide tubes, respectively.

22. The method of claim 13 further comprising removing said obturator after said tissue dilation leaving behind said cannula.

23. The method of claim 22 wherein said inserting and attaching of said first and second spine fixation elements is provided by a screwdriver configured to be inserted through said cannula.

24. The method of claim 23 wherein said screwdriver comprises a screw retention sleeve, a handle attached to a proximal end of said screw retention sleeve, a screw retention element attached to a distal end of said screw retention sleeve and a screw release/capture trigger.

* * * * *